US006036953A

United States Patent [19]

Ryan et al.

[11] Patent Number: 6,036,953

[45] Date of Patent: Mar. 14, 2000

[54] **HETEROLOGOUS ANTIGENS IN LIVE CELL *V. CHOLERAE* STRAINS**

[75] Inventors: Edward T. Ryan, Quincy; Stephen B. Calderwood, Wellesley, both of Mass.

[73] Assignee: The General Hospital Corporation, Boston, Mass.

[21] Appl. No.: 08/977,577

[22] Filed: Nov. 25, 1997

Related U.S. Application Data

[60] Provisional application No. 60/032,328, Nov. 29, 1996.

[51] Int. Cl.[7] .......................... A01N 63/00; A61K 39/00; A61K 39/02; A61K 39/08

[52] U.S. Cl. ....................... 424/93.2; 424/93.1; 424/93.4; 424/93.41; 424/192.1; 424/9.34; 424/234.1; 424/236.1; 424/261.1; 424/239.1; 424/247.1; 514/837

[58] Field of Search ................................. 424/93.1, 93.4, 424/93.2, 93.48, 192.1, 9.34, 234.1, 236.1, 200.1, 241.1, 257.1, 267.1, 261.1, 239.1; 514/837

[56] References Cited

U.S. PATENT DOCUMENTS

| | | | |
|---|---|---|---|
| 4,882,278 | 11/1989 | Mekalanos | 435/172.3 |
| 5,143,830 | 9/1992 | Holland et al. | 435/69.7 |
| 5,747,028 | 5/1998 | Calderwood et al. | 424/93.2 |

FOREIGN PATENT DOCUMENTS

| | | |
|---|---|---|
| 0 125 228 | 11/1984 | European Pat. Off. . |
| 0 251 579 | 1/1988 | European Pat. Off. . |
| 0 257 837 | 3/1988 | European Pat. Off. . |
| 0 322 237 | 6/1989 | European Pat. Off. . |
| 0 564 689 | 10/1993 | European Pat. Off. . |
| 8902924 | 4/1989 | WIPO . |
| WO 90/03437 | 4/1990 | WIPO . |
| WO 91 07979 | 6/1991 | WIPO . |
| WO 91/18092 | 11/1991 | WIPO . |
| WO 93 13202 | 7/1993 | WIPO . |
| WO 94/00493 | 1/1994 | WIPO . |
| WO 94/01533 | 1/1994 | WIPO . |
| WO 94/19482 | 9/1994 | WIPO . |
| WO 9606627 | 3/1996 | WIPO . |
| WO 96/12802 | 5/1996 | WIPO . |

OTHER PUBLICATIONS

U.S. application No. 08/403,584, Mekalanos et al, filed Mar. 14, 1996.

Gentschev et al. Infect. Immun. 60: 5091–5098, 1992.

Abstracts of the 89th Annual Meeting of the American Society for Microbiology, p. 128, 1989.

Forrest et al., Immunogenicity of a Candidate Live Oral Typhoid/Cholera Hybrid Vaccine in Humans, J. Infectious Diseases 159:145:146, 1989.

Miller and Mekalanos, Strategies for the Development of Vaccines for Typhoid Fever, Shigellosis, and Cholera, Biomedical Science and the Third World 569:145–154, 1989.

Nashar et al., Current Progress in the Development of the B Subunits of Cholera Toxin and *Escherichia coli* Heat–labile Enterotoxin . . . the Oral Delivery of Heterologous Antigens and Epitopes, Vaccine 11:235–240, 1993.

Acheson et al., Protective Immunity to Shiga–Like Toxin I Following Oral Immunization with Shiga–Like Toxin I B–Subunit–Producing *Vibrio cholerae* CVD 103–HgR, Infection and Immunity 64:355–357, 1996.

Bäckström et al., Insertion of a HIV–1–Neutralizing Epitope in a Surface–Exposed Internal Region of the Cholera toxin B–subunit, Gene p. 211–217, 1994.

Jobling et al., Fusion Proteins Containing the A2 Domain of Cholera Toxin Assemble with B Polypeptides of Cholera Toxin to Form Immunoreactive . . . Holotoxin–Like Chimeras, Infection & Immunity 60:4915–4924, 1992.

Kaper and Levine, Recombinant Attenuated *Vibrio Cholerae* Stains Used as Live Oral Vaccines, Res. Microbiol. 141:901–906, 1990.

Kaper et al., A Recombinant Live Oral Cholera Vaccine, Bio/Technology 345–349, Apr. 1984.

Pierce et al., Determinants of the Immunogenicity of Live Virulent and Mutant *Vibrio cholerae* 01 in Rabbit Intestine, Infection and Immunity 55:477–481, 1987.

Sanchez et al., Genetic Fusion of a Non–toxic Heat–Stable Enterotoxin–Related Decapeptide Antigen to Cholera Toxin B–subunit, FEBS Letters 241:110–114, 1988.

Sanchez et al., Recombinant System for Overexpression of Cholera Toxin B Subunit in *Vibrio cholerae* as a Basis for Vaccine Development, Proc. Natl. Acad. Sci. USA 86:481–485, 1989.

Schödel et al., Synthesis in *Vibrio cholerae* and Secretion of Hepatitis B Virus Antigens Fused to *Escherichia coli* Heat–labile Exterotoxin Subunit B, Gene 255–259, 1991.

Tacket et al., Cholera Vaccines, Chapter 3.

Acheson et al., "Comparison of shiga–like toxin I B–subunit expression and Localization in *Escherichia coli* and *vibrio cholerae* by using trc or iron–regulated promoter systems", Infect. & Immun. 61:1098–1104 (1993).

Mobassaleh et al., "Pathogenesis of shigella diarrhea: evidence for a developmentally regulated glycolipid receptor for shigella toxin involved in the fluid secretory response of rabbit small intestine", J. Infect. Dis. 157:1023–1031 (1988).

Cray et al., "Successful colonization and immunization of adult rabbits by oral inoculation with *vibrio cholerae* 01", Infect. and Immun. 41:735–741 (1983).

(List continued on next page.)

*Primary Examiner*—James C. Housel
*Assistant Examiner*—S. Devi
*Attorney, Agent, or Firm*—Fish & Richardson P.C.

[57] ABSTRACT

Disclosed is a *V. cholerae* cell containing a DNA encoding a fusion polypeptide that includes a heterologous antigenic polypeptide sequence such as a portion of *C. difficile* toxin A. The fusion polypeptide also includes one of the following: (i) an *E. coli* hemolysin A subunit (wich is coexpressed with sequences encoding hemolysin B and D subunits); (ii) a secretion signal sequence and cholera toxin A2 subunit (which is coexpressed with cholera toxin B subunit); or (iii) cholera toxin B subunit.

8 Claims, 13 Drawing Sheets

OTHER PUBLICATIONS

Mekalanos et al., Cholera Toxin Genes: Nucleotide Sequence, Deletion Analysis and Vaccine Developemnt, Nature 306:551–557, 1983.

Kaper et al., Recombinant Nontoxinogenic *vibrio Cholerae* Strains as Attenuated Cholera Vaccine Candidates, Nature 308:655–658, 1984.

Levine et al., Safety, Immunogenicity, and Efficacy of Recombinant Live Oral Cholera Vaccines, CVD 103 and CVD 103–HgR, Lancet 468–470, 1988.

Levine et al., Volunteer Studies of Deletion Mutants of *vibrio Cholerae* 01 Prepared by Recombinant Techniques, Infec. Immun. 56:161–167, 1988.

Herrington et al., Toxin, Toxin–Coregulated Pili, and the toxR Regulon are Essential for *Vibrio Chlerae* Pathogenesis in Humans, J. Exp. Med. 168:1487–1492, 1988.

Goldberg et al., Identification of an Iron–Regulated Virulence Determinant in *Vibrio Cholerae*, Using TnphoA Mutagenesis, Infec. Immun. 58:55–60, 1990.

Taylor et al., Use of phoA Gene Fusions to Identify a Pilus Colonization Factor Coordinately Regulated with Cholera Toxin, Proc. Natl. Acad. Sci. USA 84:2833–2837, 1987.

Taylor et al., Broad–Host–Range Vectors for Delivery of TnphoA: Use in Genetic Analysis of Secreted Virulence Determinants of *Vibrio Cholerae*, J. Bac. 171:1870–1878, 1989.

Carniel et al., Molecular Cloning, Iron–Regulation and Mutagenesis of the irp2 Gene encoding HMWP2, a Protein Specific for the Highly Pathogenic Yersinia, Mol. Micro. 6:379–388, 1991.

Keren et al., Direct Demonstration in Intestinal Secretions of an IgA Memory Response to Orally Administered Shigella Flexneri Antigens, J. Immun. 128:475–479, 1982.

Bjorn et al., Effect of Iron on Yields of Exotoxin A in Cultures of *Pseudomonas Aeruginosa* PA–103, Infec. Immun. 19:785–791, 1978.

Black et al., Protective Efficacy in Humans of Killed Whole–Vibrio Oral Cholera Vaccine with and without the B Submit of Cholera Toxin, Infec. Immun. 55:1116–1120, 1987.

Blomfield et al., Allelic Exchange in *Escherichia coli* Using the *Bacillus Subtilis* sacB Gene and a Temperature–Sensitive pSC101 Replicon, Mol. Micro. 5:1447–1457, 1991.

Calderwood et al., Nucleotide Sequence of the Shiga–Like Toxin Genes of *Escherichia coli,* Proc. Natl. Acad. Sci. USA 84:4364–4368, 1987.

Calderwood et al., A System for Production and Rapid Purification of Large Amounts of the Shiga Toxin/Shiga–Like Toxin I B Subunit, Infec. Immun. 58:2977–2982, 1990.

Calderwood and Mekalanos, Iron Regulation of Shiga–Like Toxin Expression in *Escherichia Coli* Is Mediated By the Fur Locus, J. Bac. 169:4759–4764, 1987.

Clemens et al., Impact of B Subunit Killed Whole–Cell and Killed Whole–Cell–Only Oral Vaccines . . . Illness and Mortality in an Area Endemic for Cholera, Lancet 1:375–1379, 1988.

Czerkinsky et al., Antibody–Producing Cells in Peripheral Blood and Salivary Glands after Oral Cholera Vaccination of Humans, Infec. Immun. 59:996–1001, 1991.

Daskaleros et al., Iron Uptake in *Plesiomonas Shigelloides:* Cloning of the Genes for the Heme–Iron Uptake System, Infec. Immun. 59:2706–2711, 1991.

De Grandis et al., Nucleotide Sequence and Promoter Mapping of the *Escherichia Coli* Shiga–Like Toxin Operon of Bacteriophage H–19B, J. Bac. 169:4313–4319, 1987.

De Lorenzo et al., Operator Sequences of the Aerobactin Operon of Plasmid ColV–K30 Binding the Ferric Uptake Regulation (fur) Repressor, J. Bac. 169:2624–2630, 1987.

Donnenberg and Kaper et al., construction of an eae Deletion Mutant of Enteropathogenic *Escherichia Coli* By Using a Positive–Selection Suicide Vector, Infec. Immun. 59:4310–4317, 1991.

Donohue–Rolfe et al., Pathogenesis of Shigella Diarrhea, J. Exp. Med. 160:1767–1781, 1984.

Donohue–Rolfe et al., Enzyme–Linked Immunosorbent Assay for Shigella Toxin, J. Clin. Micro. 24:65–68, 1986.

Fernandez–Beros et al., Immune Response to the Iron–Deprivation–Induced Proteins of *Salmonella Typhi* in Typhoid Fever, Infec. Immun. 57:1271–1275, 1989.

Gentry et al., Quantitative Microtiter Cytotoxicity Assay for Shigella Toxin, J. Clin. Micro. 12:361–366, 1980.

Goldberg et al., Positive Transcriptional Regulation of an Iron–Regulated Virulence Gene in *Vibrio Cholerae,* Proc. Natl. Acad. Sci. USA 88:1125–1129, 1991.

Goldberg et al., Transcriptional Regulation by Iron of a *Vibrio Cholerae* Virulence Gene and Homology of the *Escherichia Coli* Fur System, J. Bac. 172:6863–6870, 1990.

Goldberg et al., Characterization of a *Vibrio Cholerae* Virulence Factor Homologous to the Family of TonB–Dependent Proteins, Mol. Micro. 6:2407–2418, 1992.

Harari et al., Synthetic Peptides of Shiga Toxin B Subunit Induce Antibodies Which Neutralize its Biological Activity, Infec. Immun. 56:1618–1624, 1988.

Harari and Arnon et al., Carboxy–Terminal Peptides from the B subunit of Shiga Toxin Induce a Local and Parenteral Protective Effect, Mol. Immun. 27:613–621, 1990.

Herrington et al., Toxin, Toxin–Coregulated Pili, and the toxR Regulon are Essential for *Vibrio Cholerae* Pathogenesis in Humans, J. Exp. Med. 168:1487–1492, 1988.

Köster et al., Molecular Characterization of the Iron Transport System Mediated by the pJM1 Plasmid in *Vibrio Anguillarum* 775, J. Biol. Chem. 266:23829–23833, 1991.

Levine et al., Safety, Immunogenicity, and Efficacy of Recombinant Live Oral Cholera Vaccines, CVD 103 and CVD 103–HgR, Lancet 2:467–470, 1988.

Harford et al., Cholera Toxin Genes: Nucleotide Sequence, Deletion Analysis and Vaccine Development, Nature 306:551–557, 1983.

Owen et al., M Cell Transport of *Vibrio Cholerae* from the Intestinal Lumen into Peyer's Patches:A Mechanism for Antigen Sampling and for Microbial Transepithelial Migration, J. Infec. Dis. 153:1108–1118, 1986.

Pearson et al., New Attenuated Derivatives of *Vibrio Cholerae,* Res. Microbiol. 141:893–899, 1990.

Poole and Braun, Iron Regulation of Serratia Marcescens Hemolysin Gene Expression, Infec. Immun. 56:2967–2971, 1988.

Staggs and Perry, Fur Regulation in Yersinia Species, Mol. Microbiol. 6:2507–2516, 1992.

Staggs and Perry, Identification and Cloning of a Fur Regulatory Gene in *Yersinia Pestis,* J. Baciol. 173:417–425, 1991.

Svennerholm et al., Intestinal Antibody Responses After Immunization with Cholera B Subunit, Lancet 1:305–308, 1982.

Svennerholm et al., Mucosal Antitoxic and Antibacterial Immunity after Cholera Disease and After Immunization with a Combined B Subunit–Whole Cell Vaccine, J. Infec. Dis. 149:884–893, 1984.

Winner III et al., New Model for Analysis of Mucosal Innumity: . . . Hybridoma Tumors Protects Against *Vibrio Cholerae* Infection, Infec. Immun. 59:977–982, 1991.

The Journal of Infectious Diseases 157:374–377, 1988.

Dixon et al 1983 The Biology of Immunologic Disease. pp. 331–336. Sunder Associates, Inc., Sunderland Massachusetts.

Jacobs et al. 1987. Nature. vol. 327(11); 532–534.

Ryan, E.T. et al.: "Protective immunity against *C. Difficile* Toxin A induced by oral immunization with a live, attenuated *V.cholerae* vector strain" Infection & Immunity, vol. 65, No. 7 Jul. 1997, pp. 2941–2949.

Tzschascel, B.D. et al.: "An *E.coli* hemolysin transport system–based vector for the export of polypeptides: Export of Shiga–like toxin IIeB subunit by *S. typhimurim* aroA" Nature Biotechnology, vol. 14, Jun. 14, 1996 pp. 765–769.

Joan R. Butterton et al., Cloning, Sequencing, and Transcriptional Regulation of viuA, the Gene Encoding the Ferric Vibriobactin Receptor of *Vibrio cholerae,* Jun. 1992, Journal of Bacteriology, vol. 174, No. 11, pp. 3729–3738.

Goldberg MB, et al., Identification of an iron–regulated virulence determinant in *Vibrio cholerae,* using TnphoA mutagenesis. Infect Immun. 1990; 58:55–60.

Calderwood SB, et al., A system for production and rapid purification of large amounts of Shiga toxin/Shiga–like toxin I B subunit; Infect Immun. 1990; 58:2977–2982.

Goldberg MB, et al., Transcriptional regulation by iron of a *Vibrio cholerae* virulence gene and homology of the gene to the *Escherichia coli* Fur System; J. Bacteriol 1990; 172:6863–6870.

Pearson GDN, et al., New attenuated derivatives of *Vibrio cholerae;* Res. Microbiol. 1990; 141:893–899.

Goldberg MB, et al. Positive transcriptional regulation of an iron–regulated virulence gene in *Vibrio cholerae,* Proc. Natl. Acad. Sci. USA 1991; 88:1125–1129.

Goldberg MB, et al., Characterization of a *Vibrio cholerae* virulence factor homologous to the family of TonB–dependent proteins, Mol. Microbiol. 1992; 6:2407–2418.

Acheson DWK, Comparison of Shiga–like toxin I B subunit expression and localization in *Escherichia coli* and *Vibrio cholerae* by using trc or iron–regulated promoter systems, Infect Immun. 1993; 61:1098–1104.

Butterton JR, et al., Use of the *Vibrio cholerae* irgA gene as a locus for insertion and expression of heterologous antigens in cholera vaccine strains, Vaccine 1993; 11:1327–1335.

Butterton JR, et al., Heterologous antigen expression in *Vibrio cholerae* vector strains, Infect Immun 1995; 63:2689–2696.

Butterton JR, et al., *Vibrio cholerae* 01. In: Blaser MJ, Smith PD, Ravdin JI, Greenberg HB, Guerrant RL, eds. Infections of the Gastrointestinal Tract, New York: Raven Press, 1995:649–670.

Butterton JR, et al., Attenuated *Vibrio cholerae* as live vector for expression of foreign antigens, In: Levine MM, Woodrow GC, Kaper JB, Cobon GS, eds. New Generation Vaccines, 2nd Ed. New York: Marcel Dekker.

Butterton JR, et al., Development of an adult, germ–free mouse model of *Vibrio cholerae* infection.

Butterton JR, et al., Co–expression of the B subunit of Shiga–like toxin I and EaeA from enterohemorrhagic *Escherichia coli* in *Vibrio cholerae* vaccine strains. Abstracts 95th Annual Meeting of the American Society the American Society for Microbiology, 1995, No. E77.

HETEROLOGOUS ANTIGENS IN LIVE CELL *V. CHOLERAE* STRAINS

CROSS REFERENCE TO RELATED APPLICATION

This application claims priority under 35 U.S.C. §119 from provisional application U.S. Ser. No. 60/032,328, filed Nov. 29, 1996.

STATEMENT AS TO FEDERALLY SPONSORED RESEARCH

The work disclosed herein was supported in part by U.S. Public Health Service grants KO8 AI01332 and KO8 AI01386 from the National Institute of Allergy and Infectious Diseases. The U.S. Government therefore may have certain rights in the invention.

The field of the invention is genetically engineered live *V. cholerae* vaccine strains.

BACKGROUND OF THE INVENTION

Microbial pathogens that infect mammals via mucosal surfaces have caused significant morbidity and mortality in the developing world. Of particular concern are pathogens that infect the gastrointestinal, respiratory, and genitourinary systems. Many proposed, conventional systemic immunization methods have been ineffective in protecting against infections that occur via such mucosal surfaces.

THE MUCOSAL IMMUNE SYSTEMS

The immune system is thought to be functionally separated into systemic and mucosal immune compartments (Czerkinsky et al., Cellular and Molecular, 1994, 1:37–44). The mucosal immune system represents the largest immunological organ in the body. Luminal antigens are processed via M (microfold) cells, which are specialized epithelial cells found in the gastrointestinal tract and are involved in the induction of a mucosal immune response (Neutra et al., Johnson LR, ed. Physiology of the Gastrointestinal Tract, Third Edition, 1994, 685–708). Antigen processing and presentation are followed by proliferation and differentiation of IgA-committed, antigen-specific B lymphocytes that circulate via the bloodstream and populate the lamina propria of the upper respiratory, intestinal, and genitourinary tracts, as well as the salivary and mammary glands. In these effector sites, plasma cells produce antigen-specific IgA, which is then secreted across epithelial cells, acquiring secretory component in the process (Neutra et al., Johnson LR, ed., Physiology of the Gastrointestinal Tract, Third Edition, 1994, 685–708). Secretory component enhances resistance of these antibodies to proteolysis. The circulation of antigen-specific cells from one inductive site to multiple effector sites has led to the concept of a common mucosal immune system.

*Vibrio cholerae*

*V. cholerae* is a gram-negative bacterium that, in its wild-type state, causes severe, dehydrating and occasionally fatal diarrhea in humans. There are an estimated 5.5 million cases of cholera each year, resulting in greater than 100,000 deaths (Bull. W. H. O. 68:303–312, 1990). Over the last several decades, cholera has been considered to occur primarily in developing countries of Asia and Africa, but recently it has reached epidemic proportions in regions of South and Central America as well (Tauxe et al., J. Am. Med. Assn. 267:1388–1390, 1992; Swerdlow et al., J. Am. Med. Assn. 267:1495–1499, 1992).

Patients who recover from cholera infection have long-lasting, perhaps lifelong, immunity to reinfection (Levine et al., J. Infect. Dis. 143:818–820, 1981). The development of *V. cholerae* vaccines has focused on reproducing this naturally occurring immunity, but the conventional, parenteral, killed whole-cell vaccine preparation provides less than 50% protection from disease, for a duration of only 3 to 6 months (Saroso et al., Bull. W. H. O. 56:619–627, 1978; Levine et al., Microbiol. Rev. 47:510–550, 1983).

The most important virulence factor for *V. cholerae* in causing clinical disease is cholera toxin, a protein complex consisting of one A subunit and five B subunits. An internal deletion of the gene encoding the A subunit of cholera toxin (ctxA) in the classical strain 0395 produces a strain (0395-N1) that is highly immunogenic in humans (Mekalanos, 1983, Nature 306:551–557; Herrington, 1988, J. Exp. Med. 168:1487–1492; Mekalanos, U.S. Pat. No. 4,882,278, herein incorporated by reference).

*Clostridium difficile*

*Clostridium difficile* is the causative agent of pseudomembranous colitis and results in significant morbidity, mortality, and cost (Kelly et al., Gastroenterology, 1992, 102:35–40; Lyerly et al., Clin. Microbiol., 1988, Rev. 1:1–18; Mitty et al., Gastroenterologist, 1994, 2:61–69). *C. difficile* causes pseudomembranous colitis through the action of two large toxins, toxin A and toxin B, that modify Rho proteins with subsequent disruption of the actin cytoskeleton (Dillon et al., Infect. Immun., 1995, 63:1421–1426). Toxin A appears to initiate intestinal damage, to produce mucosal disruption, and to permit full cytotoxicity of toxin B (Lyerly et al., Clin. Microbiol., 1988, 1:1–18). The genes encoding toxin A and toxin B have been sequenced (Dove et al., 1990, Infect. and Immun. 58:480–488; von Esc et al., 1990, Gene 96:107–113; and von Eichel-Streiber et al., 1995, Mol. Microbiol. 17:313–321 (GenBank Accession No. Z23277)). The carboxy terminal third of toxin A, which is approximately 800 amino acids in length, is essential for toxin binding to trisaccharide receptors on human intestinal epithelial cells (Dove et al., 1990, Infect. and Immun. 58:480–488; Krivan et al., Infect. Immun., 1986, 53:573–581; Lyerly et al., Clin. Microbiol., 1988, 1:1–18; Sauerborn et al., Nucl. Acids Res., 1990, 18:1629–1630; Tucker et al., Infect. Immun., 1991, 59:73–78; von Eichel-Streiber et al., Gene, 1990, 96:107–113). Antibodies directed against toxin A prevent toxin binding, neutralize secretory and inflammatory effects, and limit or prevent clinical disease (Allo et al., Gastroenterology, 1979, 76:351–355; Corthier et al., Infect. Immun., 1991, 59:1192–1195; Johnson et al., J. Immunol., 1993, 150:117A Abstract #657; Ketley et al., J. Med. Microbiol., 1987, 24:41–52; Kim et al., Infect. Immun., 1987, 55:2984–2992; Leung et al., J. Pediatr., 1991, 118:633–637; Warny et al., Infect. Immun., 1994, 62:384–389). Antibodies specifically directed against the carboxy terminus of toxin A have been shown to prevent holotoxin binding and abrogate subsequent cytotoxic events (Corthier et al., Infect. Immun., 1991, 59:1192–1195; Frey et al., Infect. Immun., 1992, 60:2488–2492; Lyerly et al., Clin. Microbiol., 1988, Rev. 1:1–18; Wren et al., Infect. Immun., 1991, 59:3151–3155).

SUMMARY OF THE INVENTION

As described in detail below, it has now been found that a potent immune response against a heterologous antigen can be stimulated in an animal by recombinant *V. cholerae*-vaccine cells that express *E. coli* hemolysin B (HlyB) and hemolysin D (HlyD) subunits along with a fusion polypeptide that includes a heterologous antigen (e.g., all or a portion of *C. difficile* toxin A or toxin B) fused to *E. coli* hemolysin subunit A (HlyA) or a portion thereof.

An alternative means for expressing an heterologous antigen in *V. cholerae* in a way that would induce a protective immune response is by expressing both cholera toxin B subunit (either naturally or recombinantly) and a fusion polypeptide that includes a secretory signal sequence, a heterologous antigen (e.g., all or a portion of *C. difficile* toxin A or toxin B), and cholera toxin A2 subunit.

Also described herein is a third type of recombinant *V. cholerae* strain. In this case, the cells are genetically engineered to express a fusion polypeptide that includes cholera toxin B subunit fused to an antigenic portion of *C. difficile* toxin A or toxin B subunit. In a preferred *V. cholerae* cell, cholera toxin B is expressed from a tac promoter on the plasmid pETR1. To produce pETR1, ctxB, including the upstream Shine-Dalgarno sequence, was recovered from C6709 (Taylor et al., 1994, J. Inf. Dis. 170:1518–1523) by recombinant, mutagenic PCR, with introduction of a unique NheI site two amino acids downstream of the coding sequence for the CtxB leader peptide, and the resulting fragment was introduced between the EcoRI and PstI sites of pKK223-3. Cholera toxin B expressed from pETR1 is secreted to the supernatant and recognized in ELISA assays (data not shown).

Without being bound to any particular theory, it is believed that each of the *V. cholerae* strains described above allows secretion of the fusion polypeptide from the vaccine strain into the gastrointestinal tract of an immunized animal. Fusion polypeptides that include the *E. coli* hemolysin A subunit are thought to be secreted via an *E. coli* hemolysin transport system that is reconstituted in the *V. cholerae* cell. Once the heterologous antigens are present in the lumen of the immunized animal, the antigens are processed via "M" (microfold) cells, which participate in the induction of a mucosal immune response (Neutra et al., Secretory Immunoglobulin A. Induction, Biogenesis, and Function. In: Johnson, ed. Physiology of the Gastrointestinal Tract. New York: Raven Press, 1994:685–708).

The invention thus provides the above-described *V. cholerae* cells (also referred to herein as "vaccine strains"), which can be admixed with a pharmaceutically acceptable excipient in formulating *V. cholerae*-based vaccines. Also included within the invention are methods for inducing an immune response in an animal (e.g., a human) by administering to the animal one or more of the aforementioned *V. cholerae*-based vaccine strains. If desired, the *V. cholerae*-based vaccines can be administered to the animal along with an immunoadjuvant. For example, purified detoxified proteins such as detoxified cholera toxin and/or detoxified heat labile enterotoxin can be given orally as detoxified immunoadjuvants (see, e.g., Clements et al., 1995, Infect. Immun. 63:1617–1627; Rappuloi et al., 1994, Infect. Immun. 63:2356–2360). As an alternative to orally administering the detoxified immunoadjuvant to an animal, conventional molecular biology techniques can be used to express the detoxified immunoadjuvant from the V. cholerae vaccine strain administered to the animal. "Detoxified immunoadjuvants" are bacterial toxins that have been mutagenized such that they are not toxic to the cell to which they are delivered or in which they are expressed.

A variety of *V. cholerae* strains can be used as "background" strains in engineering the *V. cholerae* vaccine strains of the invention. Preferred background strains include *V. cholerae*-01 strain 569B, *V. cholerae*-01 strain 0395, and *V. cholerae*-0139 strain Bengal 2 and their vaccine derivatives. The classical *V. cholerae*-01 CA401 and El Tor 01 strain Bahrain 2 and C6709 (with its derivative Peru2) are less preferred.

"Heterologous antigenic polypeptide" is defined as an antigenic polypeptide (e.g., a naturally-occurring polypeptide) that is not naturally expressed by *V. cholerae*. It is preferably a polypeptide that is naturally expressed by an infectious organism (other than *V. cholerae*), and which induces an antigenic response in an animal (preferably a mammal such as a human, non-human primate, cow, horse, sheep, goat, pig, dog, cat, rabbit, rat, mouse, guinea pig, or hamster). If desired, the heterologous antigenic polypeptide can be a fusion polypeptide, a fragment of a protein, or a naturally-occurring or synthetic epitope.

Typically, the infectious organism is a bacterium (e.g., *Clostridium difficile*), a virus, or a eukaryotic parasite. Preferred heterologous antigenic polypeptides include, e.g., an immunogenic bacterial toxin such as *C. difficile* toxin A or B, Shiga toxin, diphtheria toxin, Pseudomonas exotoxin A, pertussis toxin, tetanus toxin, anthrax toxin, one of the *E. coli* heat-labile toxins (LTs), one of the *E. coli* heat-stable toxins (STs), or one of the *E. coli* Shiga-like toxins; an OSP (Outer Surface Protein) of *Borrelia burgdorferi*; an immunogenic, nontoxic bacterial protein such as a colonization factor of diarrheogenic *E. coli*, a colonization factor of *Bordetella pertussis*, a pilin of uropathogenic *E. coli*, or a pilin of *Neisseria gonorrhoeae*; an immunogenic viral surface protein from a virus such as human immunodeficiency virus (HIV), any of the Herpes viruses (e.g., Herpes simplex virus or Epstein-Barr virus), influenza virus, poliomyelitis virus, measles virus, mumps virus, rubella virus, rotavirus, respiratory syncytial virus, adenovirus, or papilloma virus; or an immunogenic protein derived from a eukaryotic parasite, such as the causative agent for malaria, pneumocystis pneumonia, or toxoplasmosis. One preferred example of such a protein is a malarial circumsporozoite protein. Where the heterologous antigenic polypeptide is a toxin (e.g., *C. difficile* toxin A or toxin B), a non-toxic portion of the toxin is included in the fusion polypeptide, while toxic portions are excluded.

Where the heterologous antigenic polypeptide is derived from *C. difficile* toxin A, the portion used in the fusion polypeptide is preferably a portion (e.g., at least 8 amino acids, and preferably at least 10) or all of the repeating peptide domain near the carboxy terminus of toxin A. When an antigenic portion of *C. difficile* toxin A or toxin B is fused to cholera toxin B subunit, the antigenic portion typically is 8–100 (preferably 8–20, and more preferably 10) amino acids in length. A preferred heterologous antigen derived from *C. difficile* toxin A has the amino acid sequence TIDGKKYYFN (SEQ ID NO:1). Where a heterologous antigenic polypeptide is fused to a secretion signal sequence and the cholera toxin A2 subunit, the antigenic polypeptide is typically 20 to 100, preferably 30 to 50, amino acids in length. When this heterologous antigenic polypeptide is derived from *C. difficile*, a 44 amino acid peptide from the peptide repeat sequence of toxin A provides a preferred heterologous antigen. This 44 amino acid epitope of *C. difficile* is encoded on the plasmid pCD11 (Price et al., 1987, Curr. Microbiol. 16:55–60), and is specifically bound by the monoclonal antibody PCG-4 (Dove et al., 1990, Infect. Immun. 58:480–488). Preferred secretion signal sequences for use in the invention are the secretion sequence of *E. coli* HlyA, of *E. coli* heat labile enterotoxin B subunit, of cholera toxin A subunit, and of pelB.

If desired, the nucleic acid encoding the fusion polypeptide can be functionally (or "operatively") linked to any promoter which functions in *V. cholerae* and permits expression at an acceptable level in vivo. Construction of such a functional linkage can be accomplished as described in detail below, or generally, using standard methods, by locating the desired promoter sequence sufficiently near to (and typically, though not necessarily, just upstream of) the promoterless sequence encoding the fusion polypeptide to permit the desired promoter sequence to control expression of the sequence encoding the fusion polypeptide. Functional siting of promoter sequences is well within the abilities of one of ordinary skill in the art of prokaryotic gene expression. Where the promoter naturally controls the expression of a *V. cholerae* virulence factor that is not essential for growth of the cell (e.g., an iron-regulated promoter such as that of irgA), the sequence encoding that virulence factor will preferably be deleted or otherwise mutated to prevent expression of a biologically active form of that virulence factor.

Preferably, the natural ctxA locus on the *V. cholerae* chromosome will be deleted or otherwise inactivated, so that biologically active cholera toxin cannot be expressed from the chromosome. Such deletions, mutations and insertions can readily be carried out by one of ordinary skill using the methods described herein, or other well-known, standard techniques. In preferred embodiments, the ctxA deletion is identical to that of strain 0395-N1 (Mekalanos, U.S. Pat. No. 4,882,278).

Construction of a promoter sequence adjacent to a sequence encoding a fusion polypeptide containing a given heterologous antigen-encoding sequence, and insertion of the resulting construct into a *V. cholerae* genome or a plasmid, is readily accomplished by one of ordinary skill.

The sequences encoding the desired polypeptides (e.g., the fusion polypeptides, HlyA, HlyB, HlyD, and cholera toxin B subunit) can be expressed in *V. cholerae* cells by integrating the sequences into the *V. cholerae* genome or by carrying the sequences on a plasmid that is introduced into the *V. cholerae* cell. If desired, a given *V. cholerae* cell can express one or more of these sequences from a plasmid, or the sequence can be integrated into the cell's chromosome. Conventional molecular biology techniques can be used to produce recombinant *V. cholerae* strains and plasmids for use in the invention. Methods for in vivo marker exchange, to introduce genes into the *V. cholerae* chromosome, are known to those of skill in the art (see, e.g., Butterton et al., 1995, Infect. Immun. 63:2689–2696). If desired, the *V. cholerae* strains and plasmids can contain a balanced lethal mutation (i.e., a lethal chromosomal mutation that is balanced by a gene expressed from the plasmid to overcome lethality). Such balanced lethal mutations are particularly useful when using the vaccine strains of the invention to express heterologous antigens in humans.

The *V. cholerae* cells of the invention can be said to define a vaccine strain useful, when combined with a pharmaceutically acceptable excipient suitable for oral administration, as a live-cell vaccine. Administration of such a vaccine to an animal (e.g., a human or other mammal) will provoke immunity not only to *V. cholerae*, but also to the organism from which the heterologous antigen is derived; it thus serves as a bivalent vaccine. An exemplary vaccine utilizes a *V. cholerae* strain genetically engineered to express *E. coli* HlyB and HlyD and a fusion polypeptide that includes (a) an antigenic, non-toxic portion of *C. difficile* toxin A or toxin B and (b) *E. coli* HlyA. This vaccine strain is described in detail below. Of course, the bacterial strain of the invention could be engineered to encode several heterologous antigens, each linked to an identical or different promoter, to produce a multivalent vaccine effective for simultaneously inducing immunity against a number of antigens or infectious diseases. In such strains, the various heterologous antigens form part of one or more fusion polypeptides that are expressed in the *V. cholerae* cells.

The invention offers several advantages. *V. cholerae* is a non-invasive organism that attaches selectively to intestinal M cells. Thus, the antigens are presented directly to underlying lymphoid tissues, permitting strong and long-lasting mucosal immune responses. *V. cholerae* colonizes human intestinal tissues for 7–14 days, thereby allowing for repeated antigenic presentation after a single administration of the vaccine. In addition, the vaccines of the invention can be administered orally. Thus, several problems inherent in parenteral immunization are avoided, such as the use of needles, the need for strict refrigeration of the vaccine, and the need for specially trained personnel to administer the vaccine by injection. Other features and advantages will be apparent from the detailed description provided below, and from the claims.

BRIEF DESCRIPTION OF THE DRAWINGS

FIG. 7A illustrates the results obtained following intraluminal challenge with PBS/BSA. FIGS. 7B and 7D illustrate the results obtained following intraluminal challenge with 1 μg of *C. difficile* toxin A. FIGS. 7C and 7E illustrate the results obtained following intraluminal challenge with 5 μg *C. difficile* toxin A. Intestinal segments shown in FIGS. 7A, 7B and 7C are from control animals that received *V. cholerae* 0395-NT(pMOhly1). Intestinal segments shown in FIGS. 7D and 7E are from a vaccinated animal that received *V. cholerae* 0395-NT (pETR14) expressing toxin A-HlyA. Magnification is 40X on hematoxylin-and-eosin stained sections of paraffin-imbedded tissues.

DETAILED DESCRIPTION

Figure 1A:
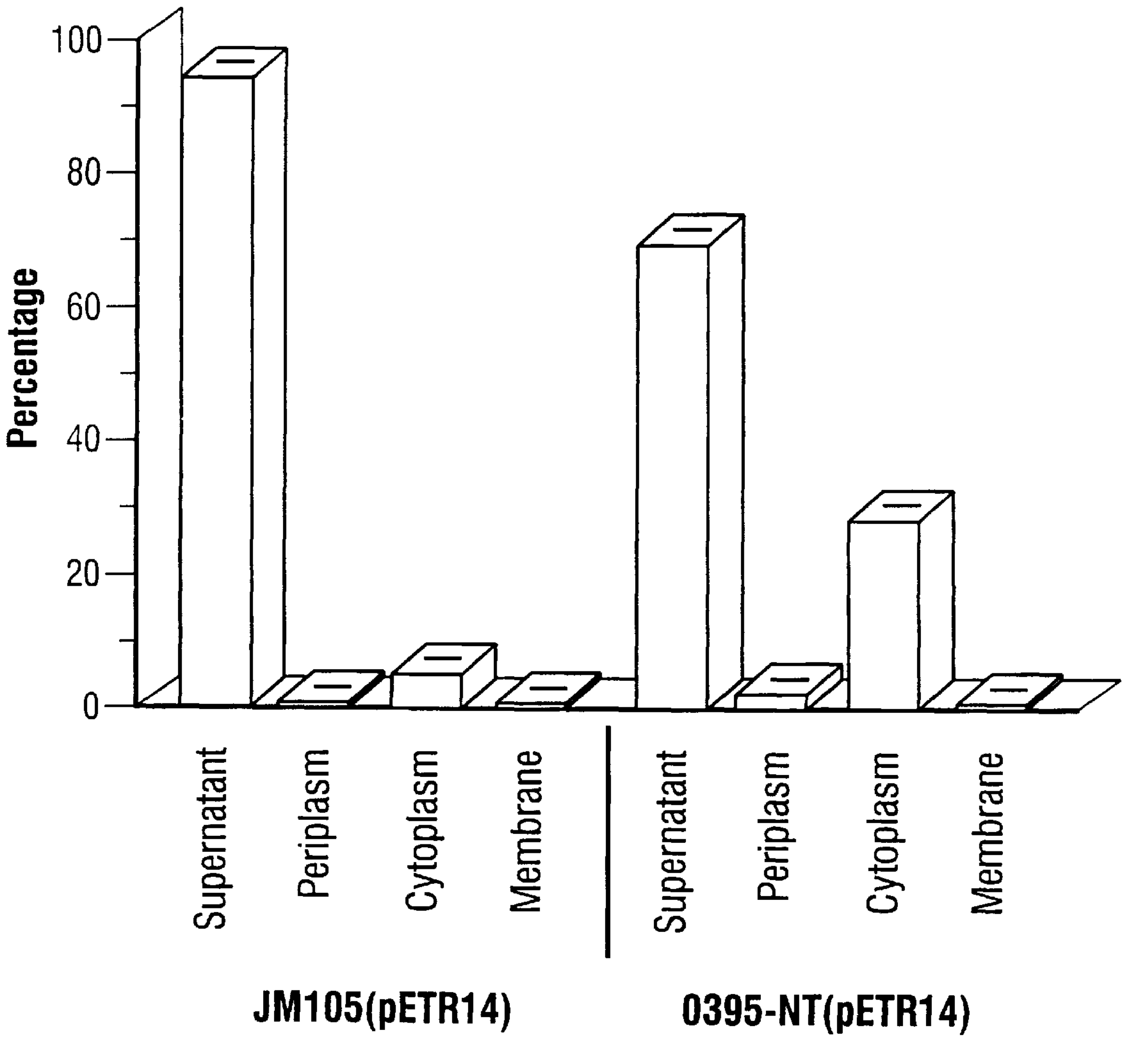
FIG. 1A is a graph depicting percentage of total toxin A protein in supernatant, cytoplasmic, periplasm, and membrane-associated fractions.

In the experiments described below in Example 1, a non-toxic, 720 amino acid portion of *C. difficile* toxin A subunit was used as a model heterologous antigen. This heterologous antigen was fused to an *E. coli* HlyA secretion signal sequence, and the resulting fusion polypeptide was co-expressed in *V. cholerae* with HlyB and HlyD. The fusion polypeptide was properly exported to the extracellular environment of *V. cholerae*, presumably by a mechanism that involves HlyB and HlyD. It was recognized by antibodies directed against *C. difficile* toxin A. When this vaccine strain was administered to rabbits, it successfully induced a protective mucosal and systemic immune response against *C. difficile* toxin A.

Examples 2 and 3 describe alternative strategies for expressing *C. difficile* toxin A epitopes in *V. cholerae*, for use in a bivalent vaccine. Example 4 describes use of such vaccines. It is noted that the *V. cholerae* cells described herein could also be used for in vitro production of the described fusion polypeptides for use in any in vitro assay (e.g., an immunoassay) requiring such a polypeptide. It is also noted that multiple plasmids encoding different fusion polypeptides with different heterologous antigenic peptide sequences could be introduced into a single *V. cholerae* strain, to produce a multivalent vaccine.

Those skilled in the art will recognize that alternative reagents and methods can be substituted for those described herein. These examples are meant to be illustrative, not limiting, as the metes and bounds of the invention are defined by the claims.

EXAMPLE 1

MATERIALS AND METHODS

Bacterial Strains, Plasmids, and Media.

The bacterial strains and plasmids are summarized in Table 1. All strains were maintained at −70° C. in Luria-Bertani broth (LB) medium (Sambrook et al., Molecular Cloning: A Laboratory Manual, 2nd Ed., 1989) containing 15% glycerol. Streptomycin (100 μg/ml), tetracycline (25 μg/ml), and ampicillin (100 μg/ml) were added as appropriate. Cultures were grown at 37° C. with aeration. Quantitative cultures were grown on thiosulfate-citrate-bile salts-sucrose (TCBS) plates or LB-agar plates containing appropriate antibiotics.

TABLE 1

Bacterial strains and plasmids

| Strain or Plasmid | Relevant genotype or phenotype | Source or reference |
|---|---|---|
| *V. cholerae* strains | | |
| O395-NT | Serotype O1, classical Ogawa, O395 ΔctxAB, $Km^r$, $Sm^r$ | a |
| O395-N1 | O1, classical, Ogawa, O395 ΔctxA, $Sm^r$ | a |
| 569B | O1, classical, Inaba, wild-type | b |
| CA401 | O1, classical, Inaba, wild-type, $Sm^r$ | c |
| C6709 | O1, El Tor, Inaba, wild-type | d, e |
| Peru2 | C6709 ΔattRS1, $Sm^r$ | d, e |
| Bahrain2 | O1, El Tor, Ogawa, E7946 ΔattRS1, $Sm^r$ | e |
| Bengal2 | Serotype O139, M010, ΔattRS1, $Sm^r$ | f |
| *E. coli* strains | | |
| JM105 | thi, rpsL, endA, sbcB15, hsdR4, supE, Δ(lac-proAB), F' [traD36, proAB$^+$, lacI$^q$, lacZ ΔM15]; $Sm^r$ | g |
| Plasmids | | |
| pcD11 | 4.7 kbp PstI fragment of *C. difficile* 10463 chromosomal DNA encoding the nontoxic carboxy terminal ⅔ of toxin A, cloned in pBR322; fragment contains an internal PstI site; $Tet^r$ | h |
| pMOhly1 | plasmid encoding the hemolysin operon of *E. coli*, with internal deletion of hlyA such that the nucleotides for the amino terminal 34 amino acids are fused with the carboxy terminal 61 amino acid HlyA secretion signal at unique NsiI site; $AP^r$ | i |
| pETR14 | 2.1 kbp PstI fragment from 3' end of insert of pCD11 encoding the nontoxic carboxy terminal ⅓ of *C. difficile* toxin A, inserted in the NsiI site of pMOhly1, in-frame between amino and carboxy termini of HlyA, $Ap^r$ | j |

$AP^r$, ampicillin resistant; $Sm^r$, streptomycin resistant; $Tet^r$, tetracycline resistant
a: Mekalanos et al., 1983, Nature 306:551–557
b: Mekalanos, 1983, Cell 35:253–263
c: Sigel and Payne, 1982, J. Bacteriol. 150:148–155
d: Taylor et al., 1994, J. Infect. Dis. 170:1518–1523
e: Butterton et al., 1995, Infect. Immun. 63:2689–2696
f: Waldor and Mekalanos, 1994, J. Infect. Dis. 170:278–293
g: Pharmacia P-L Bio-chemical Inc., Milwaukee, WI
h: Price et al., 1987, Curr. Microbiol. 16:55–60
i: Gentschev et al., 1995, Infect. Immun. 63:4202–4205
j: Described herein Genetic Methods.

Isolation of plasmid DNA, restriction enzyme digestion, agarose gel electrophoresis, and Southern hybridization of DNA separated by electrophoresis were performed according to standard molecular biological techniques (Sambrook et al., Molecular Cloning: A Laboratory Manual, 2nd Ed., 1989). DNA sequencing was performed using ABI Prism DiTerminator Cycle™ sequencing with AmpliTaq™ DNA polymerase FS employing an ABI377 DNA Sequencer (Perkin Elmer Applied Biosystems Division, Foster City, Calif.).

Plasmids were transformed into *E. coli* strains by standard techniques. Plasmids were electroporated into *V. cholerae* using a Gene Pulser™ (Bio-Rad Laboratories, Richmond, Calif.) following the manufacturers' protocol, and modified for electroporation into *V. cholerae* as previously described (Goldberg et al., Proc. Natl. Acad. Sci. USA, 1991, 88:1125–1129). Electroporation conditions were 2,500 V at 25-μF capacitance, producing time constants of 4.6–4.8 ms.

DNA restriction endonucleases, T4 DNA ligase, and calf intestinal alkaline phosphatase were used according to conventional methods, as recommended by the manufacturers. Restriction digested DNA fragments were separated on 1% agarose gels; the desired DNA fragments were cut from the gels under UV illumination and the DNA was recovered with GenElute Agarose Spin Columns (Supelco Inc., Bellefonte, Pa.).

Plasmid Construction.

Plasmid pETR14 was constructed by placing the 2.1 kbp PstI fragment of pCD11 in-frame into the compatible-overhang NsiI site of pMOhly1 treated with calf intestinal alkaline phosphatase. The ligation product was transformed into *E. coli* JM105 and confirmed by restriction enzyme digestion and sequence analysis. pETR14 was electroporated into the *V. cholerae* strains of interest and successful electroporation was confirmed by restriction enzyme digestion.

Characterization of Toxin A-HlyA.

Supernatant and intracellular fractions were produced using conventional methods. Overnight cultures (3 ml) were centrifuged at 14,000 rpm (Eppendorf Centrifuge 5415C; Brinkmann Instruments, Inc., Westbury, N.Y.) for 10 minutes. Supernatants were recovered and passed through a 0.45 μm sterile ACRODISCTM filter (Gelman Sciences, Ann Arbor, Mich.). Recovered cell pellets were washed in 1 M Tris-HC1, pH 8.0, then centrifuged for 5 minutes at 14,000 rpm, and the resulting pellets were recovered. Cell pellets were frozen at −70° C. for 30 minutes, thawed and resuspended in 1 M Tris-HCl, pH 8.0. The resuspended cell pellets were sonicated for three 5-second bursts at 60% probe intensity (Biosonik Bronwill Scientific, Rochester, N.Y.). Freeze-thawed sonicates were spun at 14,000 rpm for 30 minutes at 4° C., and the supernatant was recovered as the intracellular fraction. Supernatant and intracellular preps were used immediately or stored at −70° C.

Inmunodetection of Toxin A-HlyA.

The amount of toxin A-HlyA present in intracellular and supernatant fractions was quantified with an enzyme linked immunosorbant assay (ELISA). Briefly, serial dilutions (undiluted-1:2,185) in phosphate buffered saline-0.05% Tween 20 (PBS-T) of intracellular or supernatant samples were applied to 96-well microtiter plates. The wells of the microtiter plates were previously coated with mouse anti-*C. difficile* toxin A monoclonal antibody PCG-4 (0.4 mg/ml; TechLab, Inc., Blacksburg, Va.) in 50 mM carbonate buffer, pH 9.6, and blocked with phosphate buffered saline-1% bovine serum albumin (PBS/BSA) (Sigma Chemical Co., St. Louis, Mo.). The plates were incubated at room temperature overnight and then washed in PBS-T. A 1:4,000 dilution of polyclonal goat anti-*C. difficile* toxin A antibody (TechLab) in PBS-T was then applied. After incubating the plates at room temperature for 12 hours and washing the plates with PBS-T, a 1:6,000 rabbit anti-goat IgG antibody horse radish peroxidase conjugate (Southern Biotechnology Associates, Inc., Birmingham, Ala.) was applied for overnight room temperature incubation. Plates were then washed, and the reactions were developed with 2,2-azino-bis (3-ethyl benzthiazoline)-6-sulfonic acid (ABTS; Sigma) with 0.1% $H_2O_2$ (Sigma). The optical density at 405 nm was read in a Vmax Microplate Reader (Molecular Devices Corp., Sunnyvale, Calif.). Measured optical densities were compared with a standard curve generated by serial dilutions of purified *C. difficile* toxin A (TechLab).

Measurement of β-galactosidase Activity.

β-galactosidase activities in undiluted and 1:10 dilutions of supernatant and intracellular fractions of various *V. cholerae* strains were measured using conventional methods (Sambrook et al., 1989, Molecular cloning: a laboratory manual, 2nd Ed.) The percentages of β-galactosidase activities in intracellular versus supernatant fractions were compared with percentages of toxin A protein measured in parallel.

Inoculation of Rabbits.

Orogastric colonization of rabbits was performed as previously described (Cray et al., Infect. Immun., 1983, 41:735–741). *V. cholerae* strains were grown overnight in LB medium, pelleted, washed in PBS, and resuspended in fresh LB medium to a final concentration of $10^{10}$ cfu per ml (approximately 80% containing plasmid). Male New Zealand white rabbits (approximately 2.5 kg; 9–11 weeks old) were fasted overnight and sedated. Gastric acid was neutralized with 50 mg cimetidine per kg IV at time 0. At 20 minutes, 10 ml of a (1:1) 5% $NaHCO_3$:*V. cholerae* inoculum in LB was given using a gastric tube. At 60 minutes, 1 ml of tincture of opium was given intraperitoneally. For rabbits receiving cholera holotoxin (CT) as an immunoadjuvant, 15 mg of CT (List Biological Laboratories Inc., Campbell, Calif.) was added for each oral inoculum. Vaccinated rabbits received two oral inocula; the first on day 0, and the second on day 14. Blood was drawn on days 0, 14, 21, and 28. Bile was obtained on day 28. Three rabbits were inoculated with 0395-NT (pMOhlyl) with 15 mg CT per inoculum; three rabbits were inoculated with 0395-NT (pETR14) without CT, and three rabbits were inoculated with 0395-NT (pETR14) with 15 mg of CT per inoculum.

To judge intestinal colonization of *V. cholerae* 0395-NT (pETR14) and plasmid retention, a separate cohort of rabbits was orally inoculated once. Washed ilea from these rabbits were quantitatively examined for the presence of pETR14 on serial days as previously described (Cray et al., Infect. Immun., 1983, 41:735–741; Pierce et al., Infect. Immun., 1988, 56:142–148; Pierce et al., Infect. Immun., 1985, 813–816). Rabbits were inoculated as described above with $10^{10}$ cfu of 0395-NT (pETR14). The plasmid pETR14 contains an ampicillin resistance gene. Four rabbits received normal water and two rabbits received water containing ampicillin (1 mg/ml). Beginning on day 2, rabbits were appropriately anesthetized and then sacrificed with Fatal-Plus (Vortech Pharmaceuticals, Dearborn, Mich.) on serial days. A 10 cm segment of ileum (beginning 10 cm proximal to the mesoappendix and moving cephalad) was removed, opened, washed in PBS, weighed, and homogenized (Tissue Grinder, Corning Inc., Corning, N.Y.) in LB. The removed ileum was then quantitatively cultured on LB medium containing streptomycin (Cray et al., Infect. Immun., 1983, 41:735–741; Pierce et al., Infect. Immun., 1988, 56:142–148; Pierce et al., Infect. Immun., 1985, 813–816). After overnight incubation, colonies were replica-plated on thiosulfate-citrate-bile salts-sucrose plates and on LB medium containing ampicillin. DNA from representative colonies growing on LB medium containing ampicillin was isolated in order to confirm the presence of pETR14.

Rabbit Serum Vibriocidal Antibodies.

Serum vibriocidal antibody titers were measured in a microassay as follows. The endogenous complement activity of test sera was inactivated by heating sera at 56° C. for one hour. Fifty μl serial 2-fold dilutions (1:25–1:25,600) of test sera and PBS were placed in wells of sterile 96-well tissue culture plates. Fifty μl of a $1\times10^8$ cfu/ml culture of *V. cholerae* 0395-NT in PBS with 22% guinea pig complement (Gibco BRL Life Technologies, Gaithersburg, Md.) was added to the serum dilution and incubated for 1 hour at 37° C. A 150 μl aliquot of brain heart infusion broth (Difco Laboratories, Detroit, Mich.) was added to each well and plates were incubated for 2.5 hours at 37° C. The optical density at 600 nm was then measured. Titers were determined by determining the dilution of serum causing a 50% reduction in optical density compared with wells containing preimmune (day 0) serum.

Rabbit Serum and Biliary Antibodies to Toxin A-HlyA.

Microtiter plates (96-well) were coated with 100 ng/well of mouse monoclonal anti-*C. difficile* toxin A antibody PCG-4 (TechLab). After an overnight room-temperature incubation followed by washing, purified *C. difficile* toxin A in carbonate buffer, pH 9.6, (100 ng/well; TechLab) was added. Plates were incubated overnight, washed, and blocked with PBS/BSA. Duplicate serial dilutions of sera (1:25–1:492,075) from days 0, 14, 21, and 28 were incubated overnight. A 1:1,000 goat anti-rabbit IgG alkaline phosphatase conjugate (Sigma) in PBS/T/2% dried milk was added and plates were incubated overnight. Reactions were developed with 2 mg/ml of p-nitrophenyl phosphate (Amnesco Inc., Solon, Ohio) diluted in 1 M Tris-HCl, pH 8.0. The optical density at 405 nm was kinetically measured. Plates were read for 5 minutes at 19 second intervals and the maximum slope was reported as milli-optical density units per minute (mOD-min). End dilutions were defined as the highest dilution of day 14, 21, and 28 sera for which the kinetic reading was statistically greater ($p<0.05$) than the kinetic reading for preimmune (day 0) serum.

Serum IgA anti-toxin A-HlyA was similarly examined with a 1:1,000 goat anti-serum against rabbit IgA antibody (α chain specific; Sigma) followed by a 1:1,000 rabbit anti-goat IgG alkaline phosphatase conjugate (Sigma). Reactions were developed and read as described above.

Anti-toxin A-HlyA IgA antibody response in bile was measured in quadruplicate at a 1:100 dilution in PBS-T in 96-well microtiter assay plates previously coated with PCG-4 and toxin A. A 1:1,000 goat anti-serum against rabbit IgA (Sigma) in PBS/T/milk (2%) was followed by a 1:2,000 rabbit anti-goat IgG alkaline phosphatase conjugate. Plates were developed and read as described above.

Rabbit Ileal Loop Toxin A Challenge Assay.

Rabbit ileal loop procedures were performed as previously described (Acheson et al., Infect. Immun., 1996, 64:355–357; Formal et al., Br. J. Exp. Path., 1961, 42:504–510; Ketley et al., J. Med. Microbiol., 1987, 24:41–52; Lima et al., Infect. Immun., 1988, 56:582–588; Mitchell et al., Gut, 1986, 27:78–85). On day 28, rabbits were anesthetized. After shaving and preparing the rabbit, the rabbit's abdomen was opened with a single midline incision. Intestines were mobilized, and the duodenum was tied off. Serial 10 cm distal small intestinal segments were tied off. Short, 2 cm intervening intestinal segments were used as spacers between the 10 cm intestine segments. Mesenteric vessels and vascular arcades were avoided. A 1 ml aliquot of 1 μg *C. difficile* toxin A (TechLab) or 5 μg toxin A was instilled intraluminally into additional 10 cm intestinal segments. Installation of 1 ml of PBS/BSA or 1 ml cholera toxin (10 μg; List) into additional 10 cm intestinal segments were employed as negative and positive controls, respectively. All installations were performed in duplicate in each animal. The intestines were then replaced within the abdominal cavity and the incision closed. Animals were returned to their cages and comfortably maintained. After 12 hours, animals were appropriately anesthetized and then sacrificed. Each ileal loop segment was removed, inspected, weighed, and its length measured. The weight to length (gm/cm) ratios were calculated for each intestinal segment. Intestines were preserved in 10% formalin and histological examination was performed.

Statistics and Graphics.

Data were plotted using CA-Cricket Graph Software (Computer Associates, Garden City, NY) and statistical significance was analyzed with a two-tailed t-test for the comparison of means.

RESULTS

Construction of pETR14.

A 2160 bp PstI fragment encoding the carboxy terminus of *C. difficile* toxin A was removed from pCD11 (Price et al., Curr. Microbiol., 1987, 16:55–60) and ligated to the compatible NsiI site of pMOhly1 (Gentschev et al., Infect. Immun., 1995, 63:4202–4205) such that the toxin A sequence was in-frame with the residual upstream (encoding for 34 amino terminal HlyA amino acids) and downstream (encoding for 61 carboxy terminal HlyA amino acids) sequences of hlyA to create plasmid pETR14. This plasmid also contained *E. coli* hlyB and hlyD. pETR14 was introduced into *E. coli* JM105 and various *V. cholerae* strains including *V. cholerae* 0395-NT. 0395-NT is a vaccine strain derived from classical *V. cholerae* 0395, from which both copies of ctx have been removed (Mekalanos et al., Nature, 1983, 306:551–557).

Characterization of the Toxin A-HlyA Fusion Polypeptide.

Figure 1B:
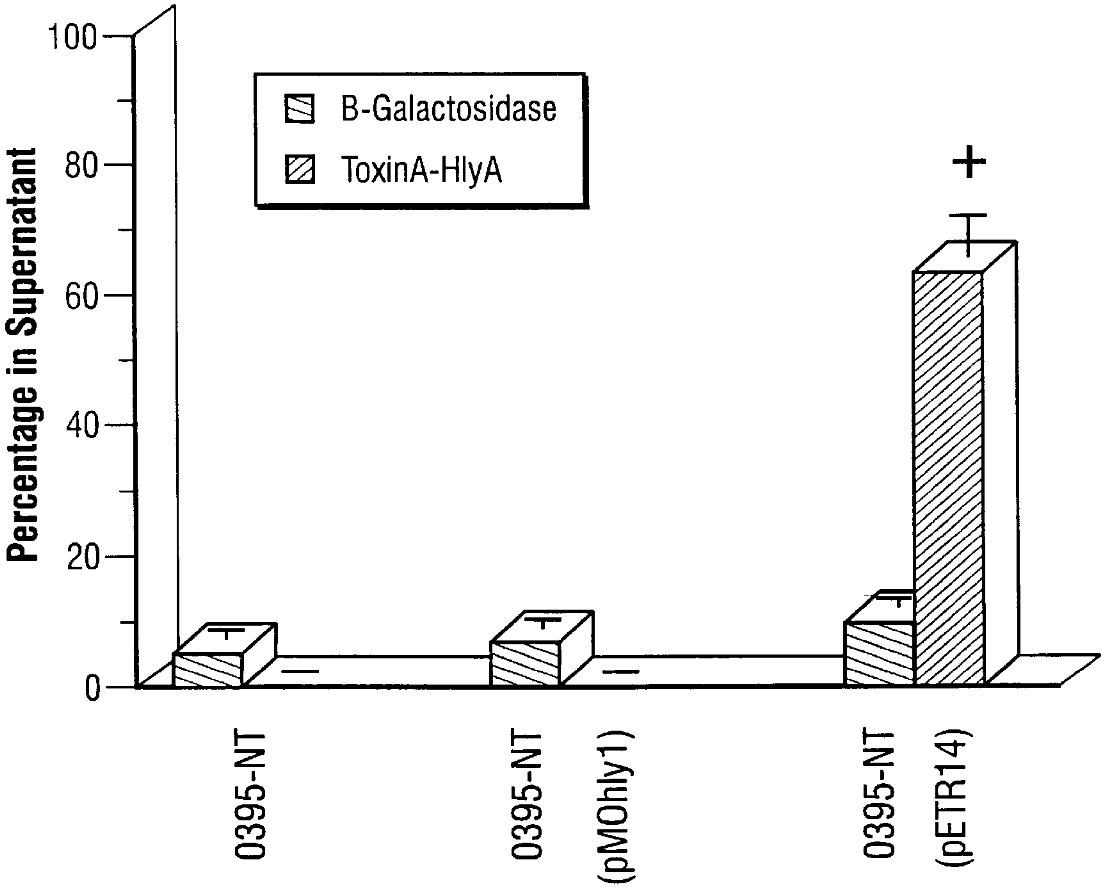
FIG. 1B is a graph representing the percentage of total toxin A protein and β-galactosidase activity in supernatant fractions.

Examination of overnight cultures disclosed that the fusion polypeptide was produced by *E. coli* JM105 (pETR14) at approximately 30–300 ng/ml/$OD_{600}$, and the fusion polypeptide was produced by *V. cholerae* 0395-NT (pETR14) at 5–50 ng/ml/$OD_{600}$. An examination of supernatants of whole cell fractions revealed that over 90% of toxin A-HlyA was localized in the supernatant in JM105 (pETR14), and over 80% was localized in the supernatant in 0395-NT (pETR14) (FIG. 1A). Simultaneous examination of β-galactosidase activity on whole cell and supernatant fractions revealed that less than 13% of total β-galactosidase activity was localized to the supernatants of *V. cholerae* 0395-NT, 0395-NT (pMOhly1), and 0395-NT (pETR14) (FIG. 1B). These data illustrate that the *E. coli* hemolysin secretory pathway can be used in *V. cholerae* to effect secretion of a fusion polypeptide that contains a heterologous antigen fused to a HlyA secretion signal sequence.

Figure 1C:
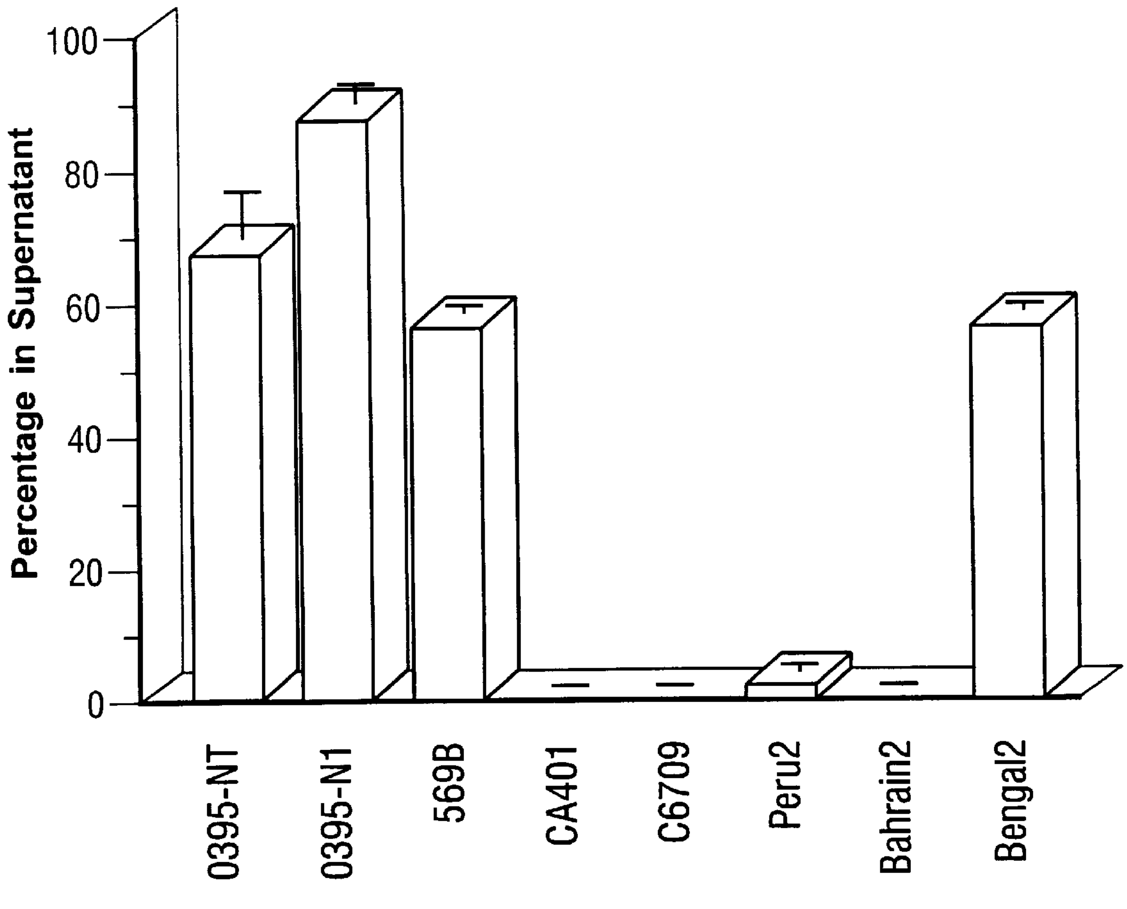
FIG. 1C is a graph representing the percentage of total toxin A protein in supernatant fractions of various *V. cholerae* strains (see Table 1 and text for details). For each graph, results are reported as geometric means, and bars depict standard errors of the mean (SEM) for each group. +, $p<0.01$, compared to the 0395-NT (pMOhlyl) control.

To further demonstrate the ability of *V. cholerae* to recognize and export heterologous antigens containing the HlyA export recognition sequence, pETR14 was introduced into a number of *V. cholerae* strains (Table 1 and FIG. 1C). Of the tested strains, *V. cholerae*-01 classical strain 569B and derivatives of *V. cholerae*-01 classical strain 0395 were the most efficient in exporting the toxin A-HlyA fusion polypeptide to the supernatant fraction. With *V. cholerae*-0139 Bengal 2, approximately 40% of the toxin A-HlyA fusion polypeptide exported to the supernatant. The classical *V. cholerae*-01 CA401 and El Tor 01 strain Bahrain 2 and C6709 (with its derivative Peru2) were less efficient exporters of the fusion polypeptide.

Intestinal Colonization of 0395-NT (pETR14) in Rabbits.

Figure 2A:
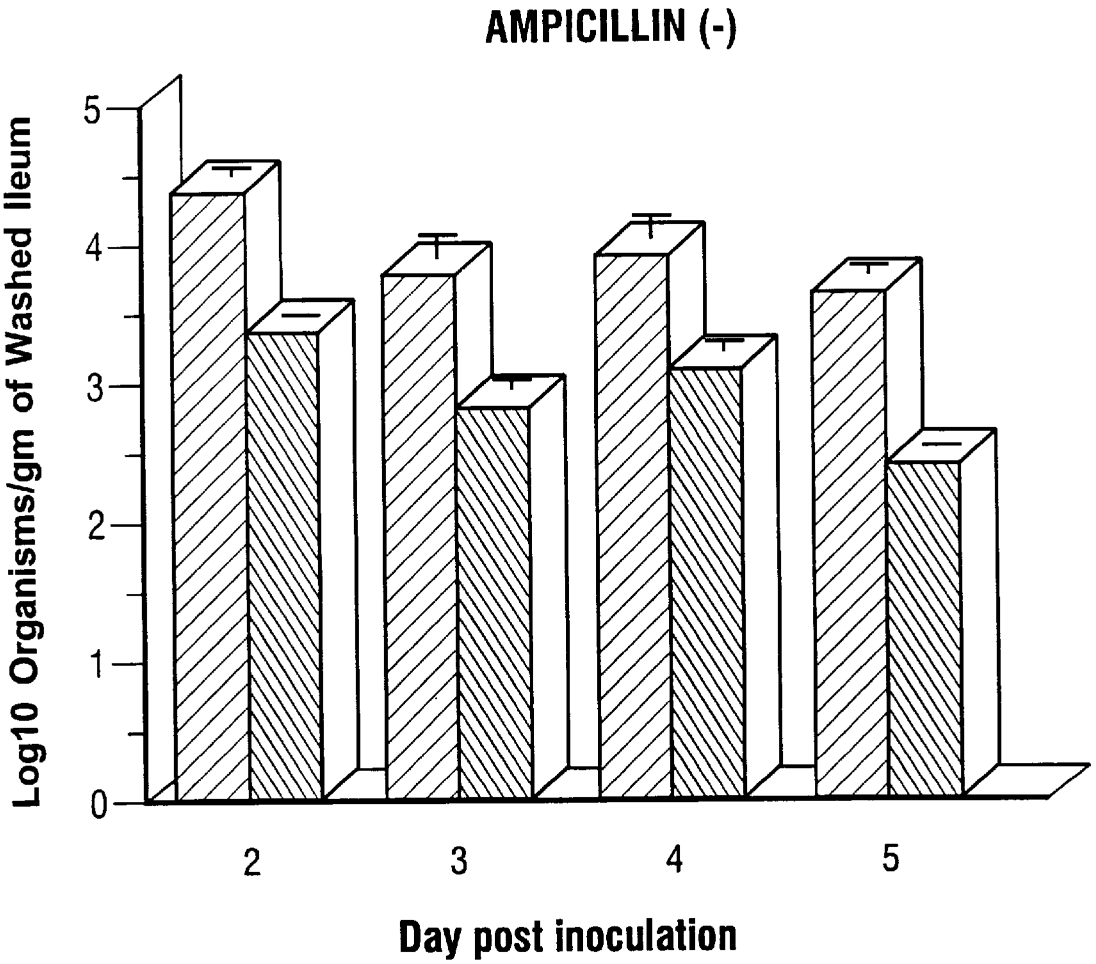
FIGS. 2A and 2B are graphs illustrating ileal colonization after oral inoculation with *V. cholerae* 0395-NT (pETR14) in rabbits treated with water that was not supplemented with ampicillin (FIG. 2A) or water supplemented with 1 mg/ml of ampicillin (FIG. 2B). Solid bars represent the geometric means titers of recovered *V. cholerae* vector, 0395-NT. Striped bars represent the titers of recovered *V. cholerae* vector still containing plasmid pETR14. Bars represent SEM for each group.
Figure 2B:
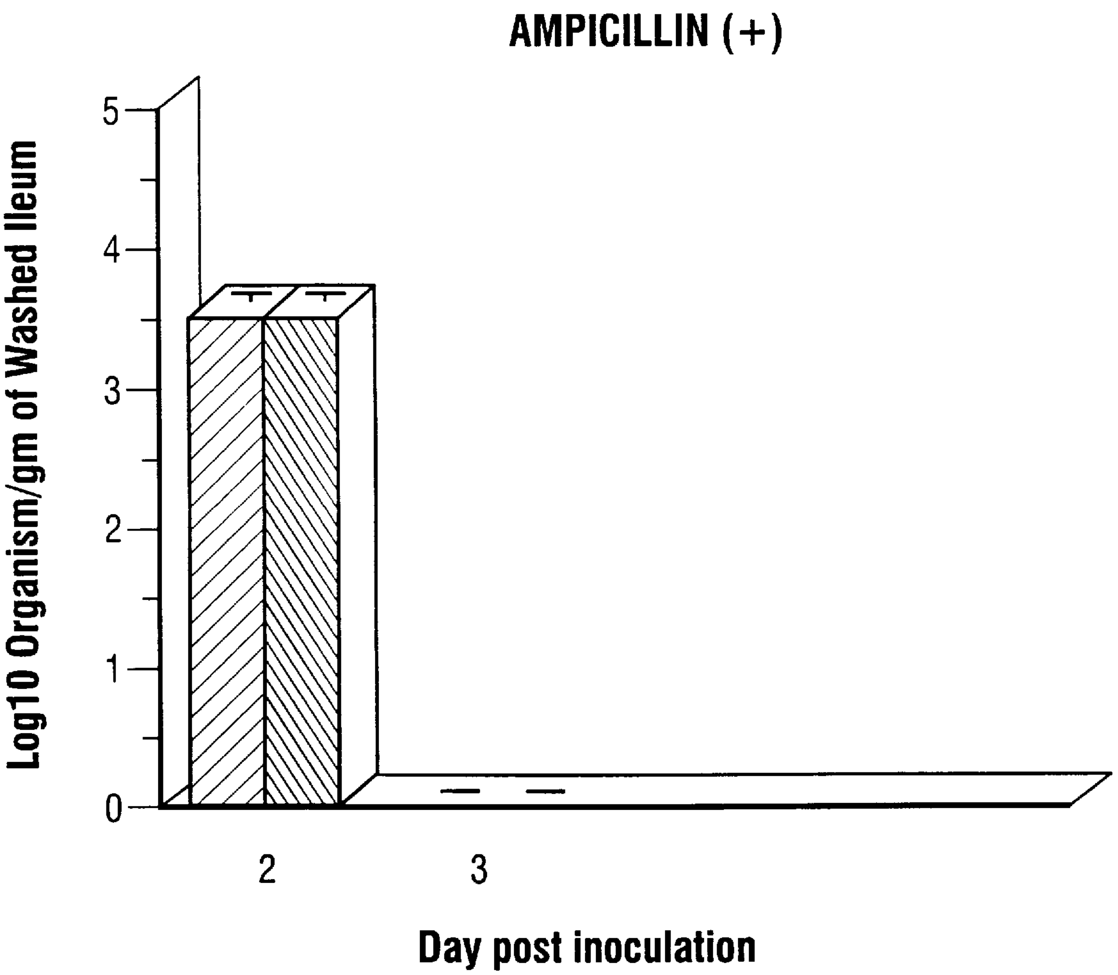

In order to investigate the duration of colonization of rabbit intestines with *V. cholerae* vaccine strains containing pETR14, quantitative cultures of washed rabbit ilea were inoculated on serial days (FIGS. 2A and 2B). The *V. cholerae* vector strains containing pETR14 slowly decreased in number over time, but were still recoverable on the last date of examination (day 5) (FIG. 2A). The addition of ampicillin (1 mg/ml) to the water supply caused a marked decrease in the recoverability of both vector *V. cholerae* and pETR14 ($Amp^r$). On day 2, the number of recoverable *V. cholerae* organisms per gm of tissue in animals treated with ampicillin was a log less than in untreated animals. Almost 100% of the recoverable isolates in the animals contained plasmid pETR14. By day 3, no *V. cholerae* vector or plasmid was recoverable in animals receiving ampicillin-supplemented water, while $10^{3-4}$ organisms per gram of ileum were still recoverable in rabbits that did not receive ampicillin (FIG. 2B). In sum, pETR14 was present for at least five days after oral inoculation. In addition, the use of antibiotics is unnecessary to allow the *V. cholerae* to colonize rabbit intestinal surfaces.

Serum Vibriocidal Responses.

Figure 3:
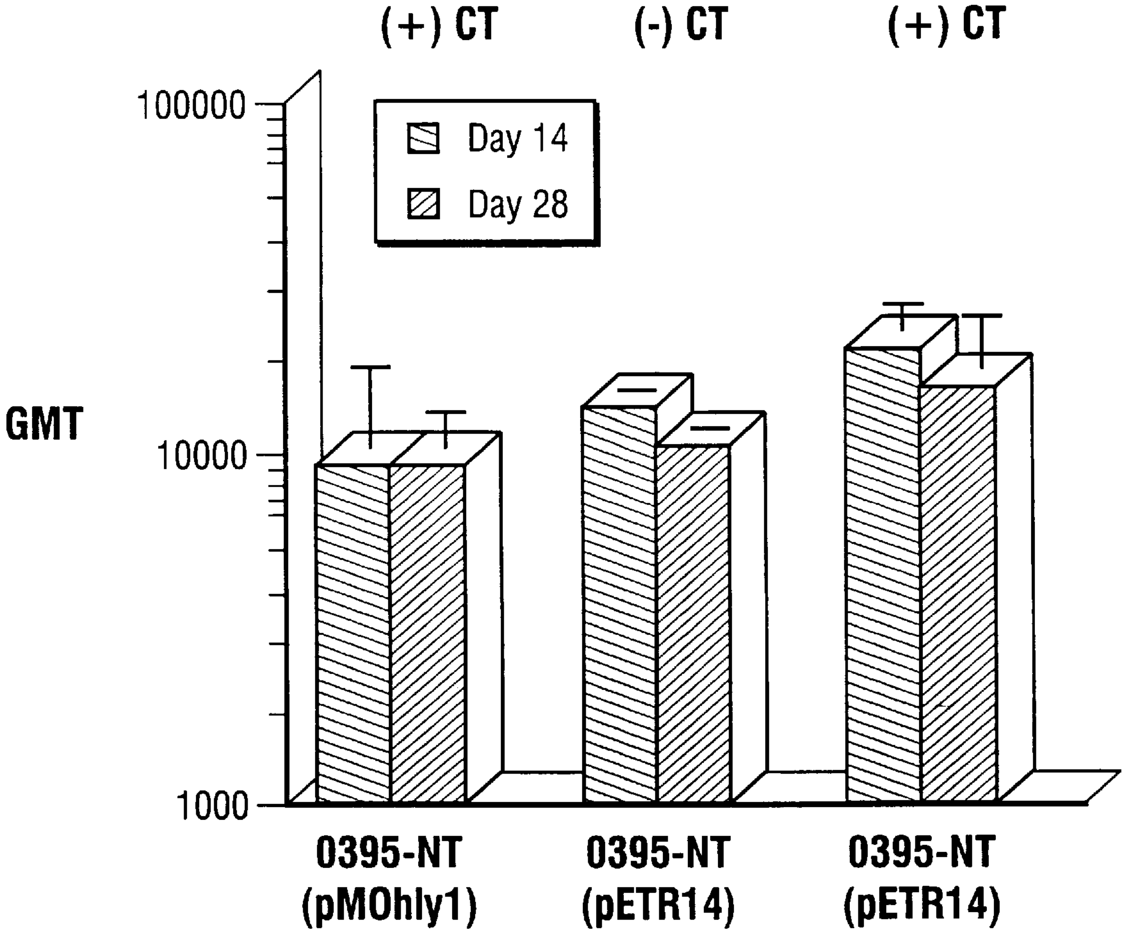
FIG. 3 is a graph showing geometric mean titers (GMT) of vibriocidal antibody responses on days 15 and 28 following inoculation of rabbits with *V. cholerae* vector strains with or without 15 μg of cholera toxin (CT) orally as an immunoadjuvant. Bars represent SEM for each group.

As determined by vibriocidal antibody titers measured on days 14 and 28, the oral immunization of rabbits was successful (FIG. 3). In this example, no appreciable booster effect was seen after day 14 reinoculation, as judged by day 28 titers, and no appreciable vibriocidal booster effect was evident in animals that received cholera holotoxin as an immunoadjuvant (FIG. 3).

Serum and Bile Antibody Responses to Toxin A-HlyA Expressed by *V. cholerae.*

Figure 4:
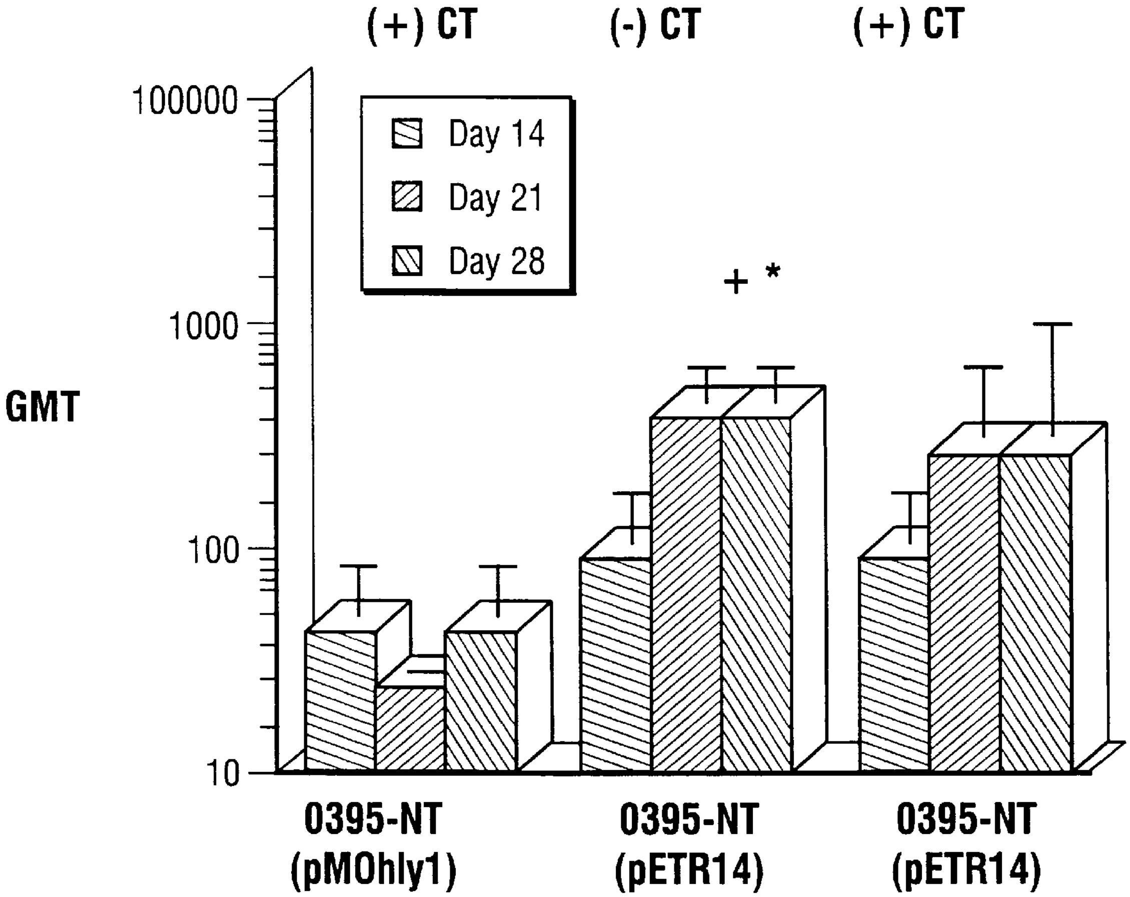
FIG. 4 is a graph illustrating serum IgG antibody responses against *C. difficile* toxin A on days 14, 21, and 28, in rabbits that received two inoculations of the indicated strains on days 0 and 14, with or without 15 μg of CT orally. Results are reported as end GMTs; bars depict SEM for each group. +, $p<0.01$; *, $p<0.05$, compared to group receiving 0395-NT (pMOhlyl).
Figure 5:
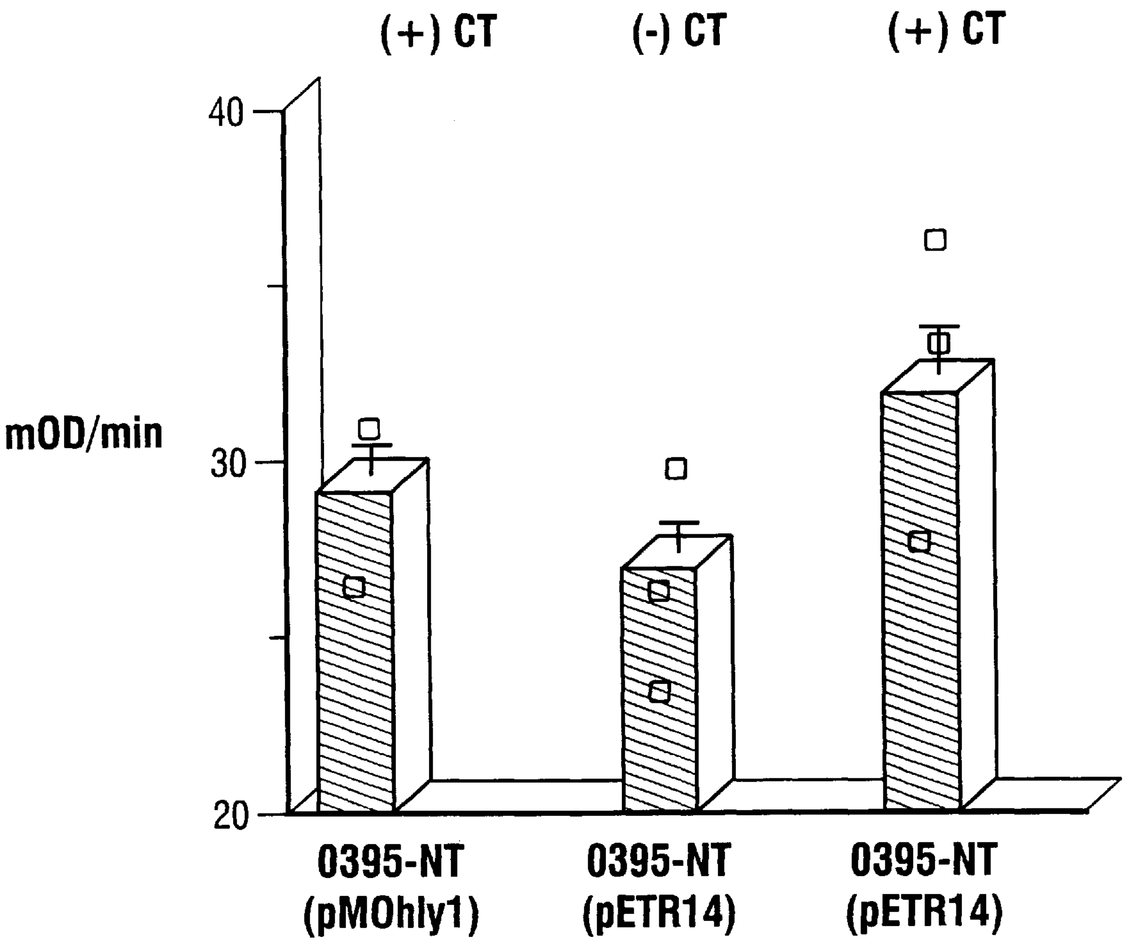
FIG. 5 is a graph representing bile IgA antibody responses against *C. difficile* toxin A on day 28 in rabbits that received two oral inoculations of the indicated strains on days 0 and 14, with or without 15 μg of CT orally. Results were determined by a kinetic ELISA reading; squares represent data points (mOD/min) from individual animals. The geometric means plus SEMs for each group are shown.

Animals inoculated with *V. cholerae* 0395-NT expressing the toxin A-HlyA fusion polypeptide from pETR14 produced significant day 21 ($p<0.01$) and day 28 ($p<0.05$) serum IgG anti-*C. difficile* toxin A antibody titers (FIG. 4). The most prominent serum IgG anti-toxin A antibody response was detected in serum of an animal that received 0395-NT (pETR14) with cholera toxin as an immunoadjuvant (end geometric mean titer (GMT) 1:2,085). Although a significant serum IgG response was detected, no appreciable serum IgA response was detected (data not shown). The most prominent IgA anti-toxin A antibody responses in bile was seen among those animals that received pETR14 in the presence of cholera toxin (FIG. 5).

Protection from the Action of *C. difficile* Toxin A in the Rabbit Ileal Loop Challenge Assay.

Figure 6A:
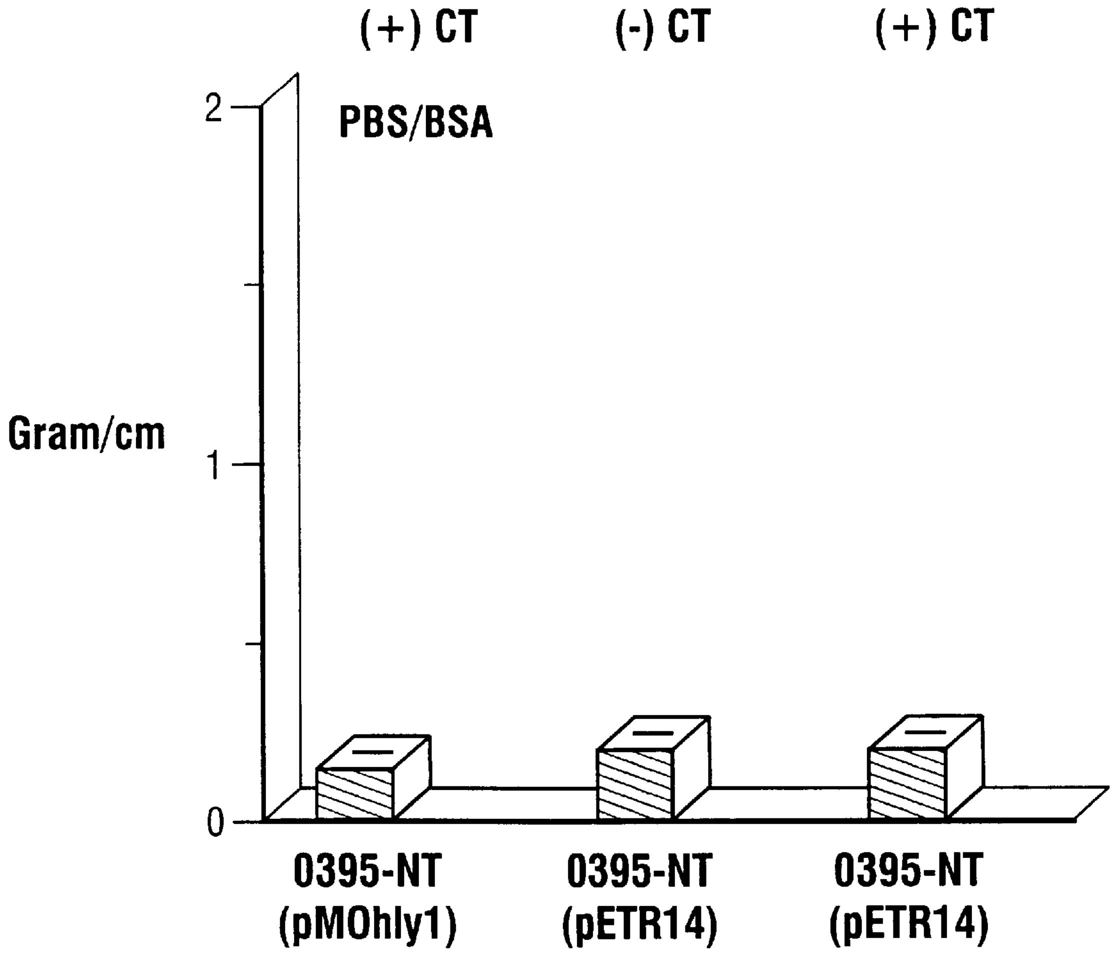
FIGS. 6A–6D are a series of graphs illustrating protection against *C. difficile* toxin A in an ileal loop challenge assay, following oral inoculation with various strains on days 0 and 14, with or without 15 μg of CT administered orally. Fluid secretory responses in ileal loops (weight/length) were measured 12 hours after intraluminal administration of PBS/BSA (FIG. 6A), 10 μg of cholera toxin (FIG. 6B), 1 μg of *C. difficile* toxin A (FIG. 6C), or 5 μg of toxin A (FIG. 6D). Results are reported as the geometric means of the secretory response; bars represent the SEM for each group. +, p<0.01; *, p<0.05, compared to vaccination with 0395-NT (pMOhly1).
Figure 6B:
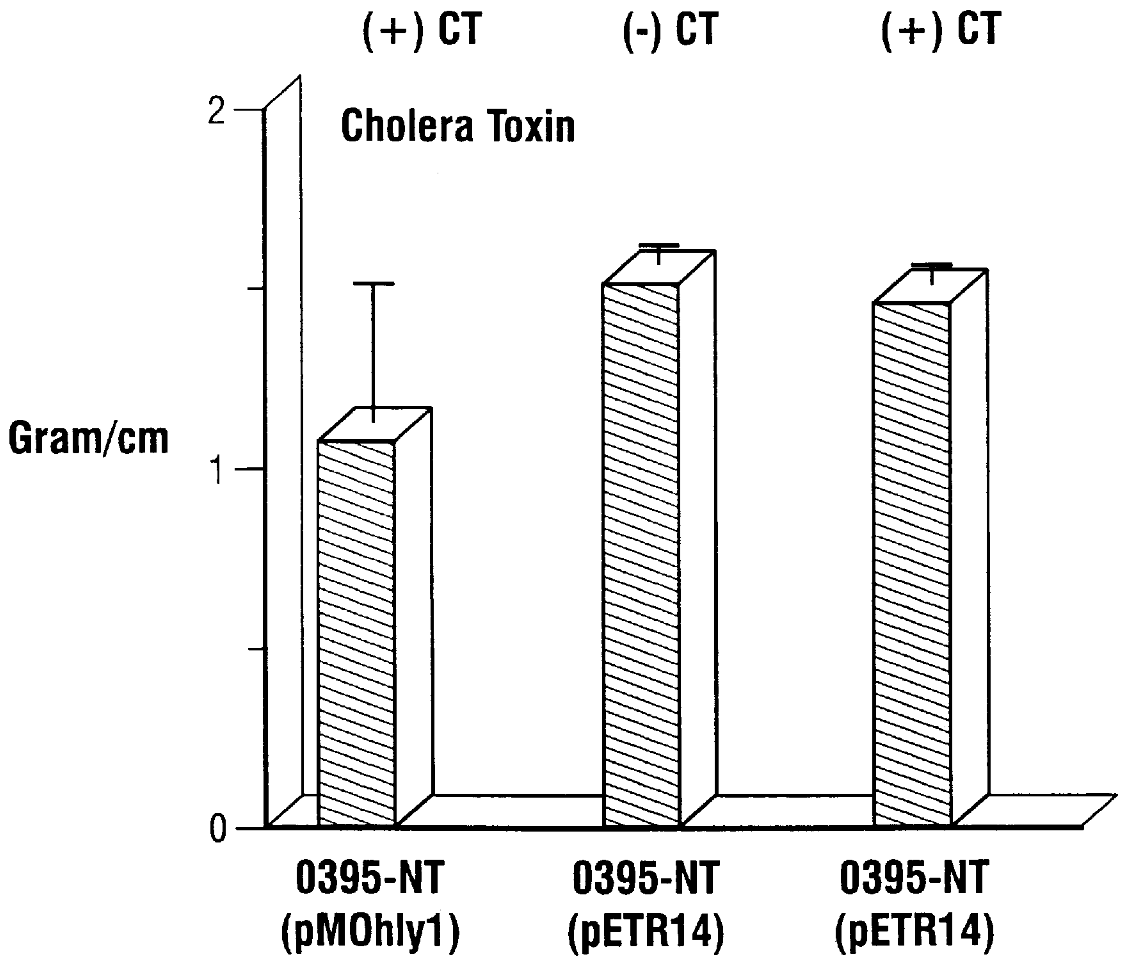
Figure 6C:
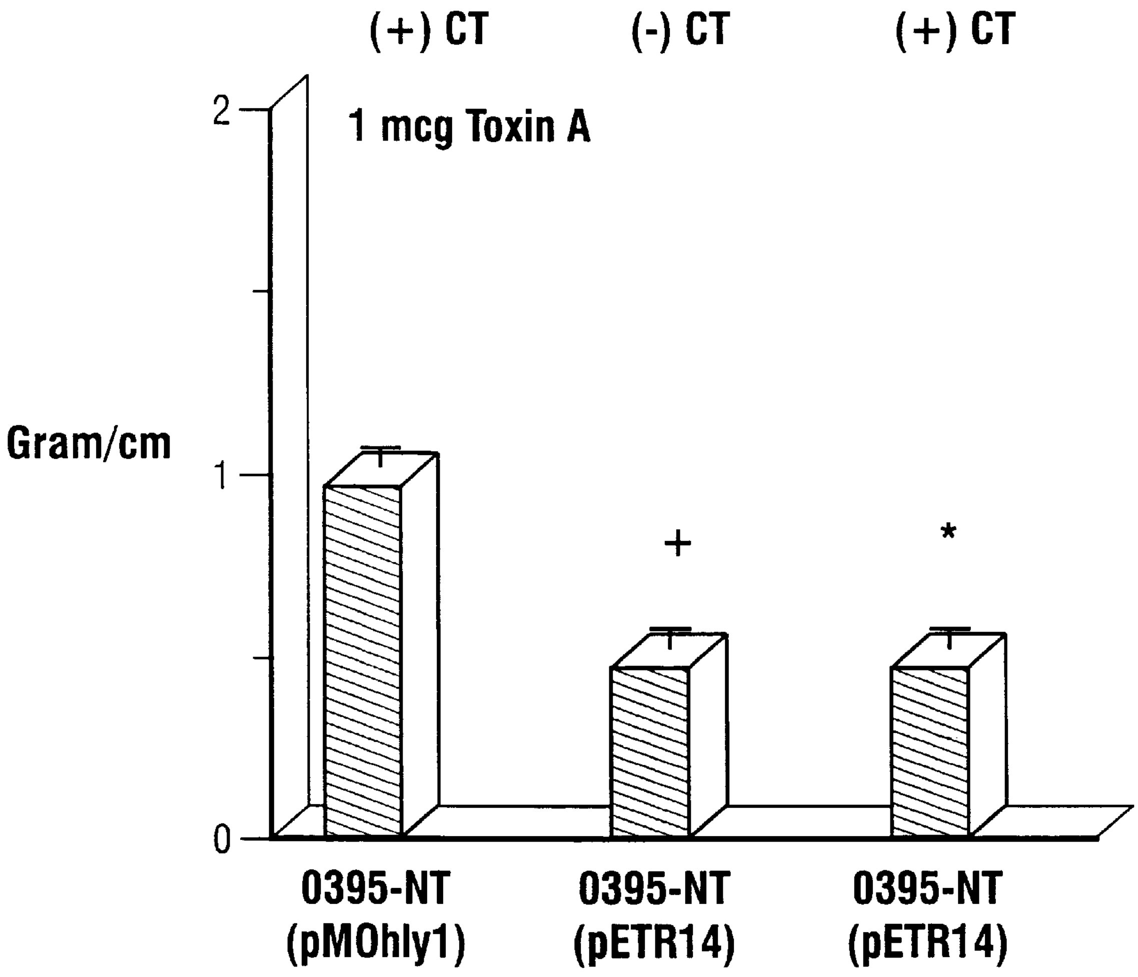
Figure 6D:
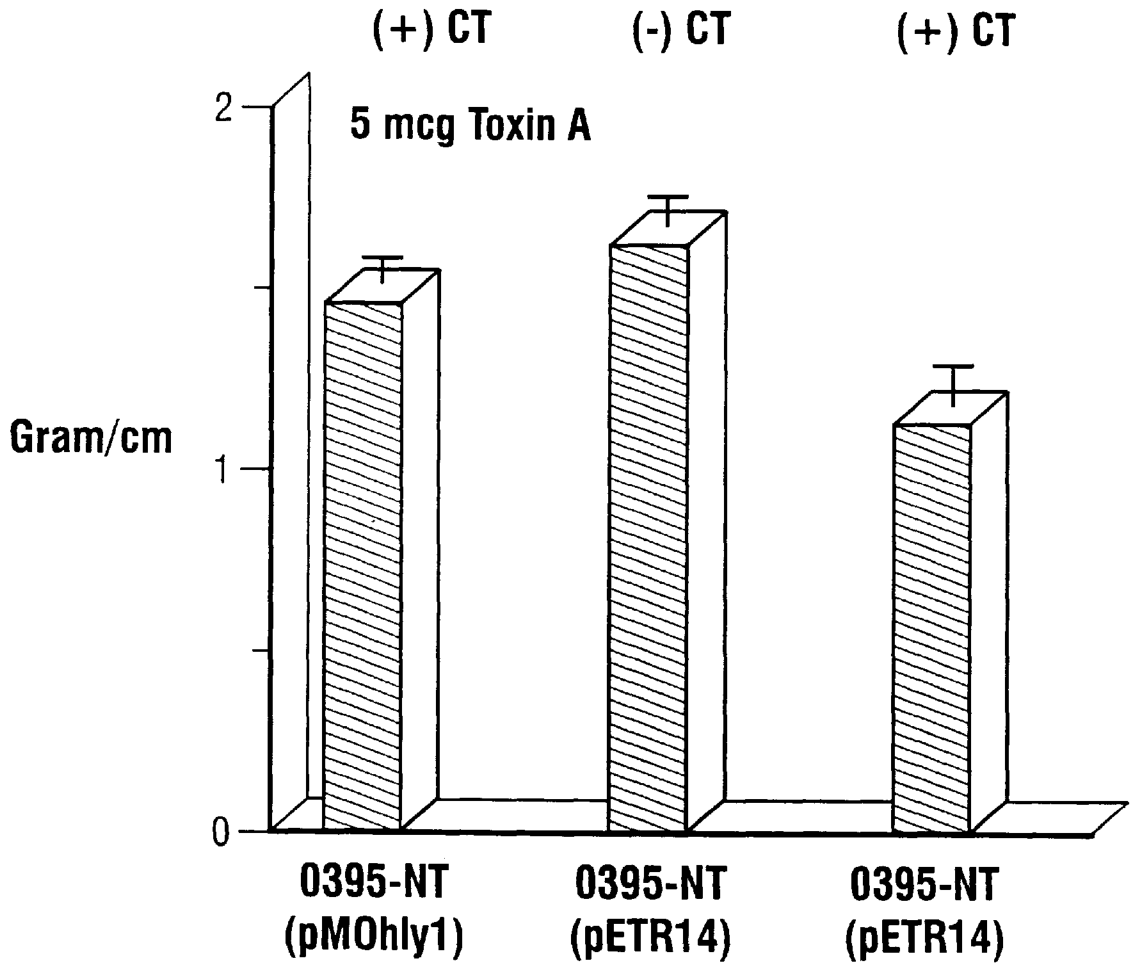

Responses to PBS/BSA (negative control) and 10 μg of cholera toxin (positive control) were similar among all groups of animals tested (see FIGS. 6A and 6D). Examination of intestinal segments into which 1 μg of *C. difficile* toxin A had been instilled revealed significant reductions in weight/length ratios in animals that received 0395-NT (pETR14) either with ($p<0.05$) or without ($p<0.01$) immunoadjuvantative cholera toxin (see FIG. 6B). The level of protection was less marked in intestinal segments that received 5 μg of toxin A, although a mild reduction in the weight/length ratio was detected in animals that received 0395-NT (pETR14) with immunoadjuvantative cholera holotoxin (FIG. 6C). Thus, these results indicate that 0395-NT (pETR14) provides an immunoprotective effect in animals challenged with *C. difficile* toxin A.

Figures 7A, 7B, 7C, 7D, 7E:
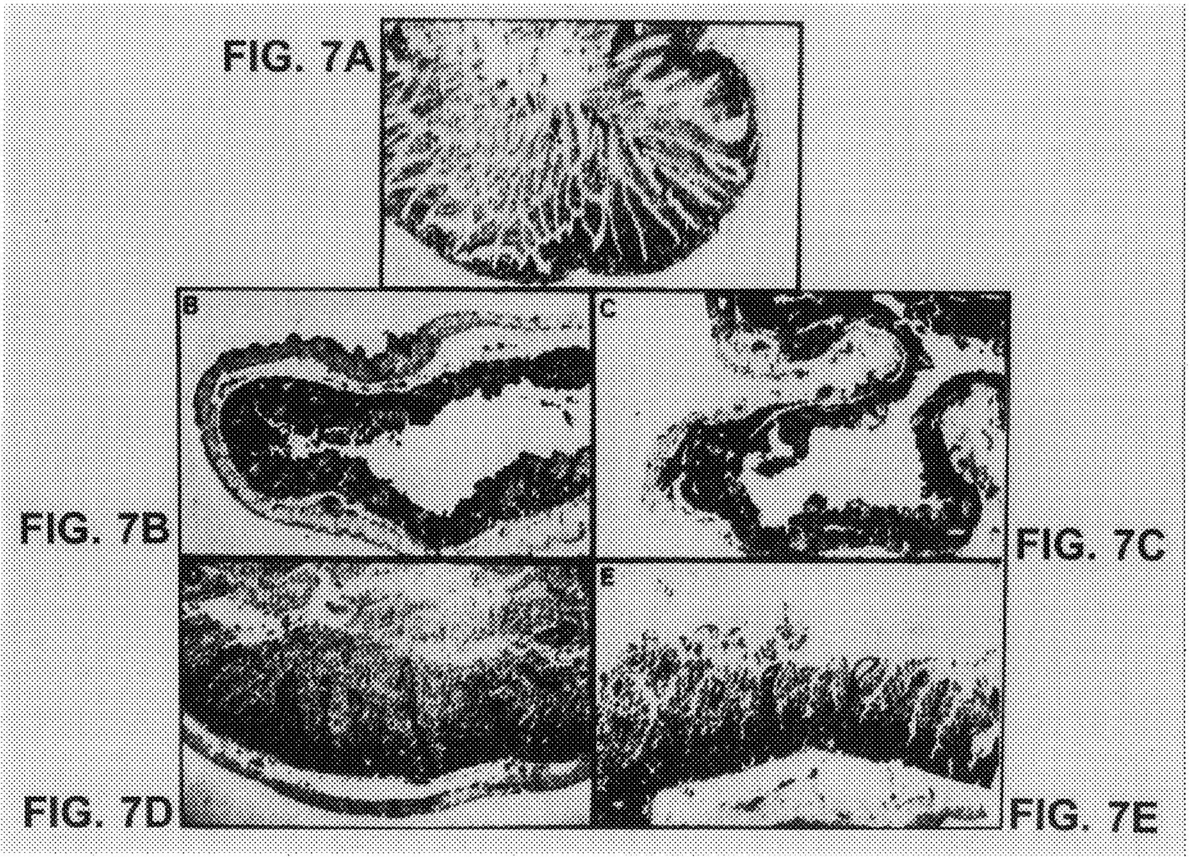
FIGS. 7A–7E are a series of photographs of histological sections of ilea recovered from vaccinated and control animals.

Histological examination was performed on intestinal segments from the control animals and from the vaccinated animal that had the most prominent anti-*C. difficile* toxin A serological response prior to challenge. Examination of ileal segments challenged with PBS/BSA revealed normal intestinal architecture in all animals examined (FIG. 7A). Histological examination of ileal segments after challenge with cholera toxin revealed no necrosis or cellular damage; however, there was splaying of intestinal villi in all animals examined, a finding consistent with the marked fluid secretory response induced by cholera toxin (FIG. 7B). Histological results obtained following challenge with *C. difficile* toxin A varied, depending on the dose of toxin A used, and on the vaccination status of the examined animal. Intestinal segments from control animals challenged with toxin A exhibited marked histological changes. In control animals challenged with 1 μg of toxin A, there was severe villous necrosis, with almost complete loss of villous height. Residual villous structures were markedly edematous and hemorrhagic. Multifocal crypt necrosis was present. The muscularis mucosae was intact, but prominent edema and vascular congestion were present in the submucosa (FIG. 7B). Following challenge with 1 μg of toxin A, intestinal segments from the vaccinated animal exhibited only partial villous necrosis, with preservation of over 50% of villous height. Although crypt areas containing mild architectural distortions were present, no deeper hemorrhagic or necrotic areas were detected (FIG. 7D).

Challenge of control animals with 5 μg of toxin A produced total villous necrosis in ileal loops (FIG. 7C). Edema and hemorrhage were prominent. Extensive crypt necrosis was present with complete loss of crypts focally. Areas of focal necrosis were also present in the muscularis mucosae. The submucosa was markedly edematous, hemorrhagic and necrotic. The muscularis externa contained extensive hemorrhage, and there was pronounced separation of the longitudinal and circular muscular layers by edema and hemorrhage. In contrast, histological examination of intestinal segments following challenge of the vaccinated animal with 5 μg of toxin A reveal only subtotal villous necrosis with villous hemorrhage (FIG. 7E). There were focal areas of crypt hemorrhage and necrosis; other structures were unremarkable. The histological changes observed in intestinal segments of the vaccinated animal following challenge with 5 μg of toxin A were thought to be equivalent to the histological changes observed in the intestinal segments of control animals following challenge with the five-fold lower dose (1 μg) of toxin A. The fact that toxin A-induced intestinal damage was reduced but not completely eliminated in this particular vaccinated animal could be due to the high potency of even small amounts of this toxin in the ileal loop assay, to suboptimal immunological responses to toxin A in vaccinated animals, or to both possibilities. Nonetheless, the results indicate that large polypeptide epitopes fused to the secretion signal of *E. coli* HlyA can be secreted by *V. cholerae* in the presence of HlyB and HlyD, and the invention can be used to induce protective immunity in mammals against the heterologous antigen *C. difficile* toxin A.

EXAMPLE 2

A second way of introducing a *C. difficile*-derived heterologous antigen into a *V. cholerae* vaccine strain involves generation of a fusion polypeptide containing an epitope derived from *C. difficile* toxin A or toxin B fused to the amino terminus of cholera toxin B subunit (CtxB). An oligonucleotide encoding the epitope (TIDGKKYYFN, SEQ ID NO:1) is synthesized with an NheI half site added at either end, and is inserted into a CtxB-encoding construct containing an NheI restriction site just downstream of the sequence encoding the signal sequence cleavage site in CtxB. This leaves the peptide epitope inserted two residues from the amino terminus of mature CtxB. Following transformation, individual transformants are screened by PCR, using primers that generate an approximately 150 bp fragment across the NheI site in the starting plasmid and looking for the expected increase in size of approximately 30 bp in the correct construct. The plasmids from transformants appearing correct by PCR are confirmed by DNA sequencing. The construct is introduced into *V. cholerae* cells (e.g., strain Peru 2) using in vivo marker exchange into lacZ of *V. cholerae*. Expression and secretion of the fusion polypeptide can be assessed by immunological techniques, employing antibodies specific for CtxB and for the *C. difficile* toxin A or toxin B epitope.

EXAMPLE 3

A third way to express a *C. difficile* toxin A or toxin B epitope in *V. cholerae* is by fusing the epitope to the nontoxic $A_2$ portion of the *V. cholerae* toxin A subunit, $CtxA_2$, and co-expressing this fusion polypeptide with CtxB. The CtxB can be naturally expressed from a chromosome of the cell, or can be encoded by a recombinant plasmid. This fusion is conveniently carried out using a DNA encoding a 44 amino acid segment of the peptide repeat region of *C. difficile* toxin A, which segment is recognized by a commercially available monoclonal antibody PCG-4 (TechLab, Blacksburg, Va.). The plasmid encodes $ctxA_2$ and ctxB cloned between unique XhoI and Bpu1102 I sites. Upstream of the XhoI site is a unique Nco I site, which is situated at the end of a pelB signal sequence. (Any signal sequence which functions in *V. cholerae* can be used.) The heterologous epitope-encoding sequence with NcoI and XhoI sites at the appropriate ends is inserted between and in frame with the signal sequence coding region and the $ctxA_2$ coding region. CtxB is separately translated from its own Shine-Dalgarno sequence in this plasmid. Transformants are screened by PCR and sequenced. The plasmid is then introduced into a *V. cholerae* vaccine strain. Expression is assessed in vitro and in vivo.

EXAMPLE 4

The *V. cholerae* strains of the invention are useful as vaccines capable of inducing immunity to a heterologous antigen(s) derived from an infectious organism. Because the strains are attenuated (i.e., do not induce a significant toxic reaction in the vaccinee), they can be used as live-cell vaccines, permitting effective immunity to result from administration of a single dose of the vaccine. An effective oral dose of the vaccine would contain approximately $10^6$ to $10^{10}$ bacteria in a volume of approximately 150 ml liquid. The diluent used would typically be water or an aqueous solution, such as 2 grams of sodium bicarbonate dissolved in 150 ml distilled water, which may be ingested by the vaccinee at one sitting, either all at once or over any convenient period of time.

What is claimed is:

1. A *V. cholerae* cell containing DNA encoding:

(A) *E. coli* HlyB, (B) *E. coli* HlyD, and (C) a fusion polypeptide, wherein the fusion polypeptide comprises:

(i) an antigenic part, or all, of an antigenic *C. difficile* polypeptide; and (ii) an *E. coli* HlyA secretion signal sequence.

2. The *V. cholerae* cell of claim 1, wherein the antigenic *C. difficile* polypeptide is an immunogenic *C. difficile* toxin.

3. The *V. cholerae* cell of claim 2, wherein the immunogenic *C. difficile* toxin is *C. difficile* toxin A or *C. difficile* toxin B.

4. The *V. cholerae* cell of claim 3, wherein the immunogenic *C. difficile* toxin is *C. difficile* toxin A and the fusion polypeptide comprises an antigenic part of the carboxy terminal third of *C. difficile* toxin A.

5. The *V. cholerae* cell of claim 1, wherein the *V. cholerae* cell does not express biologically active cholera toxin A subunit.

6. The *V. cholerae* cell of claim 1, wherein the background strain of the *V. cholerae* cell is selected from the group consisting of *V. cholerae*-01 strain 569B, *V. cholerae*-01 strain 0395, and *V. cholerae*-0139 strain Bengal 2.

7. The *V. cholerae* cell of claim 1, wherein the DNA further encodes a detoxified immunoadjuvant.

8. The *V. cholerae* cell of claim 7, wherein the detoxified immunoadjuvant is detoxified cholera toxin or detoxified heat labile enterotoxin.

* * * * *